US012661027B2

(12) United States Patent
Chang et al.

(10) Patent No.: US 12,661,027 B2
(45) Date of Patent: Jun. 23, 2026

(54) ELECTRONIC DEVICE CONFIGURED TO COMPENSATE FOR ERROR IN BIOIMPEDANCE VALUE

(71) Applicant: Samsung Electronics Co., Ltd., Gyeonggi-do (KR)

(72) Inventors: Namseok Chang, Gyeonggi-do (KR); Younghyun Kim, Gyeonggi-do (KR); Seungmin Lee, Gyeonggi-do (KR)

(73) Assignee: Samsung Electronics Co., Ltd. (KR)

( * ) Notice: Subject to any disclaimer, the term of this patent is extended or adjusted under 35 U.S.C. 154(b) by 1406 days.

(21) Appl. No.: 17/416,111

(22) PCT Filed: Oct. 14, 2019

(86) PCT No.: PCT/KR2019/013440
§ 371 (c)(1),
(2) Date: Jun. 18, 2021

(87) PCT Pub. No.: WO2020/138667
PCT Pub. Date: Jul. 2, 2020

(65) Prior Publication Data
US 2022/0071503 A1      Mar. 10, 2022

(30) Foreign Application Priority Data

Dec. 24, 2018    (KR) ........................ 10-2018-0168337

(51) Int. Cl.
*A61B 5/053* (2021.01)
*A61B 5/00* (2006.01)

(52) U.S. Cl.
CPC .............. *A61B 5/053* (2013.01); *A61B 5/681* (2013.01); *A61B 5/6898* (2013.01); *A61B 5/7225* (2013.01); *A61B 2562/046* (2013.01)

(58) Field of Classification Search
CPC ....... A61B 5/053; A61B 5/681; A61B 5/6898; A61B 5/7225; A61B 2562/046
See application file for complete search history.

(56) References Cited

U.S. PATENT DOCUMENTS

| | | | |
|---|---|---|---|
| 10,555,686 B1* | 2/2020 | Kimoto ................ | A61B 5/0535 |
| 2011/0208458 A1* | 8/2011 | Pinter ................... | A61B 5/053 |
| | | | 702/65 |

(Continued)

FOREIGN PATENT DOCUMENTS

| | | |
|---|---|---|
| EP | 2 974 652 | 1/2016 |
| EP | 3 335 631 | 6/2018 |

(Continued)

OTHER PUBLICATIONS

PCT/ISA/210 Search Report issued on PCT/KR2019/013440, Jan. 22, 2020, pp. 5.

(Continued)

*Primary Examiner* — Jason M Sims
*Assistant Examiner* — Ari S Padda
(74) *Attorney, Agent, or Firm* — The Farrell Law Firm, P.C.

(57) ABSTRACT

According to various embodiments, an electronic device may comprise: a biological body contact circuit including four electrodes; a current-voltage measurement module including a power supply port, a current measurement port, a first voltage measurement port, a second voltage measurement port, an alternating current signal generator electrically connected to the power supply port, an ammeter electrically connected to the current measurement port, and a voltmeter interposed between and electrically connected to the first voltage measurement port and the second voltage measurement port; a processor; a memory electrically connected to the processor to store the characteristic impedance values of circuit elements interposed between and electrically con- (Continued)

nected to the current-voltage measurement module and the biological body contact circuit, and to store values for parasitic impedance stemming from parasitic elements existing between the biological body contact circuit and a ground; and a current-voltage path configuration module configured to electrically connect the biological body contact circuit to the power supply port, the current measurement port, the first voltage measurement port, and the second voltage measurement port such that the voltage path and current path of the biological body contact circuit can be changed under control of the processor. Various other embodiments are also possible.

15 Claims, 22 Drawing Sheets

(56) References Cited

U.S. PATENT DOCUMENTS

| | | | | |
|---|---|---|---|---|
| 2014/0154649 A1* | 6/2014 | Farley | ............... | A61B 5/6898 |
| | | | | 434/236 |
| 2014/0276166 A1 | 9/2014 | Dror et al. | | |
| 2016/0015290 A1 | 1/2016 | Kim et al. | | |
| 2016/0128604 A1* | 5/2016 | Eom | .................... | A61B 5/681 |
| | | | | 600/384 |
| 2017/0100052 A1* | 4/2017 | Jung | .................... | A61B 5/086 |
| 2018/0020945 A1 | 1/2018 | Woo | | |
| 2018/0172793 A1* | 6/2018 | Passoni | .............. | A61B 5/6801 |
| 2018/0206761 A1 | 7/2018 | Jung et al. | | |
| 2021/0003523 A1 | 1/2021 | Chandak et al. | | |

FOREIGN PATENT DOCUMENTS

| | | |
|---|---|---|
| EP | 3 351 169 | 7/2018 |
| JP | 2015-002779 | 1/2015 |
| KR | 10-2016-0009982 | 1/2016 |
| KR | 10-2017-0041511 | 4/2017 |
| KR | 10-2018-0009431 | 1/2018 |
| KR | 10-2018-0010719 | 1/2018 |
| KR | 10-2018-0087043 | 8/2018 |
| KR | 10-2020-0072263 | 6/2020 |

OTHER PUBLICATIONS

PCT/ISA/237 Written Opinion issued on PCT/KR2019/013440, Jan. 22, 2020, pp. 3.
Mazzeo, Brian A., "Parasitic capacitance influence of potential-sensing electrodes on four-electrode liquid impedance measurements", J. Appl. Phys. 105, 094106 (2009), . . . https://doi.org/10.1063/1.3124365, pp. 6.
Mazzeo, Brian A. et al., "Two- and four-electrode, wide-bandwidth, dielectric spectrometer for conductive liquids: Theory, limitations, and experiment", J. Appl. Phys. 102, . . . 104106 (2007); https://doi.org/10.1063/1.2815666, pp. 7.
Pelc, Damjan et al., "Four-contact impedance spectroscopy of conductive liquid samples", Rev. Sci. Instrum. 82, 073907 (2011); . . . https://doi.org/10.1063/1.3609867, pp. 6.
Grimnes, Sverre et al., "Sources of error in tetrapolar impedance measurements on biomaterials and other ionic conductors", J. Phys. D: Appl. Phys. 40 (2007) 9-14.
Brigati, S. et al., "Active Compensation of Parasitic Capacitances for Very High Frequency CMOS DACs", IEEE International Symposium on Circuits and Systems (1993), pp. 4.
European Search Report dated Jan. 4, 2022 issued in counterpart application No. 19904090.8-1113, 9 pages.

* cited by examiner

ELECTRONIC DEVICE CONFIGURED TO COMPENSATE FOR ERROR IN BIOIMPEDANCE VALUE

PRIORITY

This application is a National Phase Entry of PCT International Application No. PCT/KR2019/013440 which was filed on Oct. 14, 2019, and claims priority to Korean Patent Application No. 10-2018-0168337, which was filed on Dec. 24, 2018, the content of each of which is incorporated herein by reference.

TECHNICAL FIELD

Various embodiments of the disclosure relate to an electronic device configured to measure a bioimpedance by using an electrode.

BACKGROUND ART

An electronic device may acquire biometric information related to the health care of a user. For example, the electronic device may include a bio-contact circuit having four electrodes, may apply an electric signal to the bio-contact circuit, and may measure the current and voltage of the bio-contact circuit by an ammeter and a voltmeter. The electronic device may acquire a bioimpedance value by using the current/voltage measurement value. Based on the acquire biometric information, the electronic device may provide the user with various types of heath information (for example, heart rate information, blood glucose information, or stress information), or may provide exercise coaching based on the biometric information.

DISCLOSURE OF INVENTION

Technical Problem

If four electrodes contact a living body, parasitic components unintended in the circuit design stage may exist between respective electrodes and the ground. An impedance resulting from such a parasitic component may cause a leakage of an electric signal. For this reason, a bioimpedance measurement error may occur.

According to various embodiments of the disclosure, an electronic device may compensate for a leakage of an electric signal resulting from a parasitic component during bioimpedance measurement, thereby acquiring an accurate bioimpedance value.

Solution to Problem

According to various embodiments, an electronic device may include: a bio-contact circuit including four electrodes; a current-voltage measurement module including a feeding port, a current measurement port, a first voltage measurement port, a second voltage measurement port, an alternating-current signal generator electrically connected to the feeding port, an ammeter electrically connected to the current measurement port, and a voltmeter electrically connected between the first voltage measurement port and the second voltage measurement port; a processor; a memory electrically connected to the processor and configured to store a characteristic impedance value of a circuit element electrically connected between the current-voltage measurement module and the bio-contact circuit and to store a value of parasitic impedance caused by a parasitic component existing between the bio-contact circuit and a ground; and a current-voltage path configuration module configured to electrically connect the bio-contact circuit to the feeding port, the current measurement port, the first voltage measurement port, and the second voltage measurement port such that a voltage path and a current path on the bio-contact circuit are changed under the control of the processor, wherein the memory stores instructions which, when executed, cause the processor to: control the current-voltage path configuration module to sequentially configure a first current-voltage path, a second current-voltage path, a third current-voltage path, and a fourth current-voltage path in the bio-contact circuit such that, in connection with each of the current-voltage paths, one of two electrodes of the voltage path matches with one of two electrodes of the current path, and no bio-impedance is included on the voltage path; receive, from the current-voltage measurement module, first current/voltage values measured in a state in which the first current-voltage path constitutes the bio-contact circuit, and obtain a first impedance measurement value by using the first current/voltage values; receive, from the current-voltage measurement module, second current/voltage values measured in a state in which the second current-voltage path constitutes the bio-contact circuit, and obtain a second impedance measurement value by using the second current/voltage values; receive, from the current-voltage measurement module, third current/voltage values measured in a state in which the third current-voltage path constitutes the bio-contact circuit, and obtain a third impedance measurement value by using the third current/voltage values; receive, from the current-voltage measurement module, fourth current/voltage values measured in a state in which the fourth current-voltage path constitutes the bio-contact circuit, and obtain a fourth impedance measurement value by using the fourth current/voltage values; correct the first impedance measurement value, the second impedance measurement value, the third impedance measurement value, and the fourth impedance measurement value by using the characteristic impedance value and the parasitic impedance value, so as to obtain contact impedance values of the four electrodes, respectively; control the current-voltage path configuration module to configure a fifth current-voltage path in the bio-contact circuit such that one of two electrodes of the fifth voltage path matches with one of two electrodes of the fifth current path, and the bio-impedance is included on the fifth current path and the fifth voltage path; receive, from the current-voltage measurement module, fifth current/voltage values measured in a state in which the fifth current-voltage path constitutes the bio-contact circuit, and obtain a fifth impedance measurement value by using the fifth current/voltage values; and acquire the bio-impedance value by using contact impedance values of electrodes located on at least the fifth voltage path among the contact impedance values, the fifth impedance measurement value, the characteristic impedance value, and the parasitic impedance value.

Advantageous Effects of Invention

According to various embodiments of the disclosure, an electronic device can correct errors of contact impedance measurements values of four electrodes, respectively, resulting from a parasitic impedance, and can acquire accurate bio-impedance values by using the corrected values.

BRIEF DESCRIPTION OF DRAWINGS

FIG. 3 is a circuit diagram of a path configuration module according to various embodiments of the disclosure:

FIG. 5A illustrates a current-voltage path configured in a bio-contact circuit according to a first control signal of Table 1.

FIG. 6A illustrates a current-voltage path configured in a bio-contact circuit according to a second control signal of Table 1.

FIG. 7A illustrates a current-voltage path configured in a bio-contact circuit according to a third control signal of Table 1.

FIG. 8A illustrates a current-voltage path configured in a bio-contact circuit according to a fourth control signal of Table 1.

FIG. 9A illustrates a current-voltage path configured in a bio-contact circuit according to a fifth control signal of Table 1.

MODE FOR THE INVENTION

Figure 1:
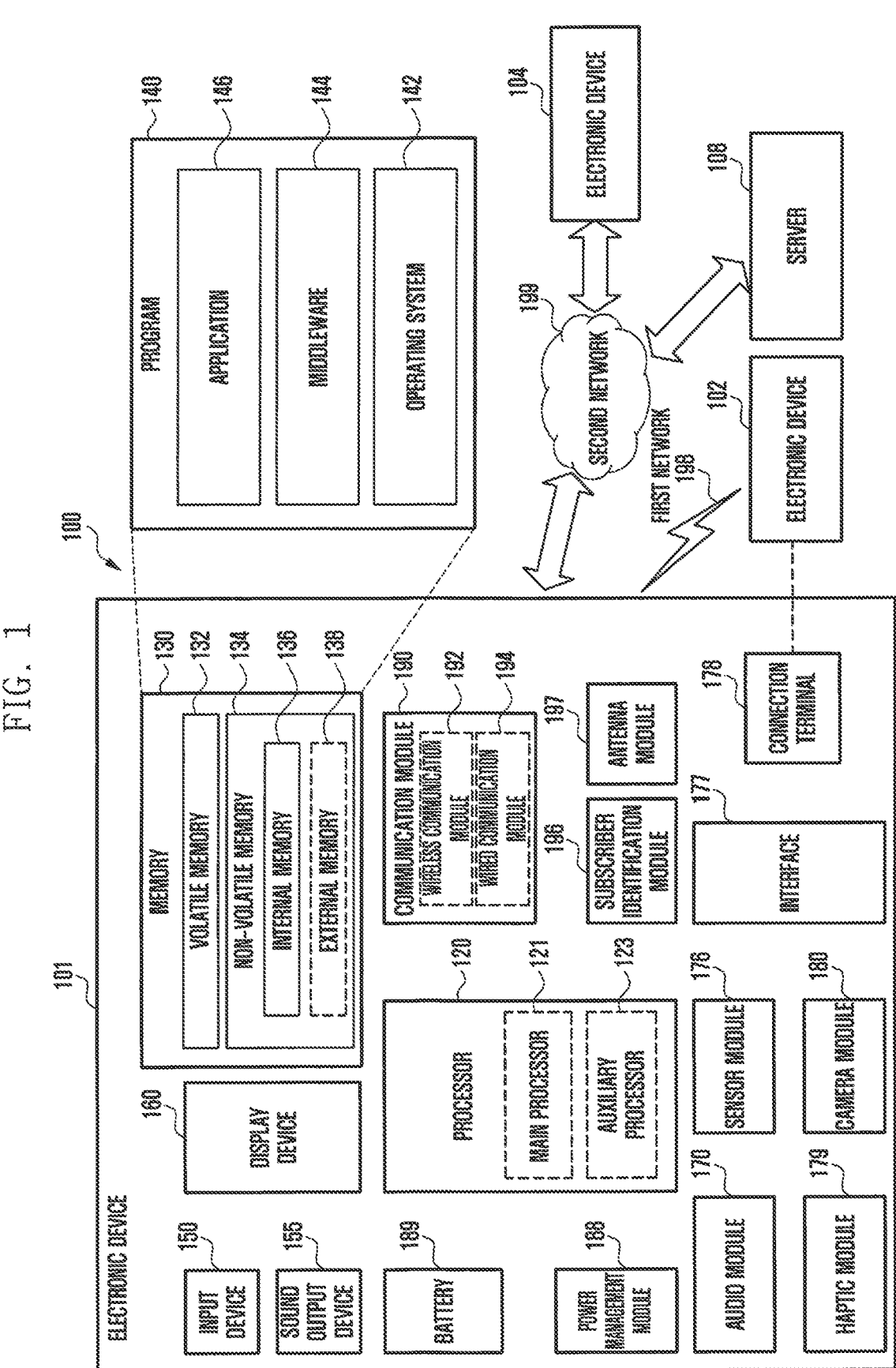
FIG. 1 illustrates an electronic device in a network environment according to various embodiments.

FIG. 1 is a block diagram illustrating an electronic device 101 in a network environment 100 according to various embodiments. Referring to FIG. 1, the electronic device 101 in the network environment 100 may communicate with an electronic device 102 via a first network 198 (e.g., a short-range wireless communication network), or an electronic device 104 or a server 108 via a second network 199 (e.g., a long-range wireless communication network). According to an embodiment, the electronic device 101 may communicate with the electronic device 104 via the server 108. According to an embodiment, the electronic device 101 may include a processor 120, memory 130, an input device 150, a sound output device 155, a display device 160, an audio module 170, a sensor module 176, an interface 177, a haptic module 179, a camera module 180, a power management module 188, a battery 189, a communication module 190, a subscriber identification module(SIM) 196, or an antenna module 197. In some embodiments, at least one (e.g., the display device 160 or the camera module 180) of the components may be omitted from the electronic device 101, or one or more other components may be added in the electronic device 101. In some embodiments, some of the components may be implemented as single integrated circuitry. For example, the sensor module 176 (e.g., a fingerprint sensor, an iris sensor, or an illuminance sensor) may be implemented as embedded in the display device 160 (e.g., a display).

The processor 120 may execute, for example, software (e.g., a program 140) to control at least one other component (e.g., a hardware or software component) of the electronic device 101 coupled with the processor 120, and may perform various data processing or computation. According to one embodiment, as at least part of the data processing or computation, the processor 120 may load a command or data received from another component (e.g., the sensor module 176 or the communication module 190) in volatile memory 132, process the command or the data stored in the volatile memory 132, and store resulting data in non-volatile memory 134. According to an embodiment, the processor 120 may include a main processor 121 (e.g., a central processing unit (CPU) or an application processor (AP)), and an auxiliary processor 123 (e.g., a graphics processing unit (GPU), an image signal processor (ISP), a sensor hub processor, or a communication processor (CP)) that is operable independently from, or in conjunction with, the main processor 121. Additionally or alternatively, the auxiliary processor 123 may be adapted to consume less power than the main processor 121, or to be specific to a specified function. The auxiliary processor 123 may be implemented as separate from, or as part of the main processor 121.

The auxiliary processor 123 may control at least some of functions or states related to at least one component (e.g., the display device 160, the sensor module 176, or the communication module 190) among the components of the electronic device 101, instead of the main processor 121 while the main processor 121 is in an inactive (e.g., sleep) state, or together with the main processor 121 while the main processor 121 is in an active state (e.g., executing an application). According to an embodiment, the auxiliary processor 123 (e.g., an image signal processor or a communication processor) may be implemented as part of another component (e.g., the camera module 180 or the communication module 190) functionally related to the auxiliary processor 123.

The memory 130 may store various data used by at least one component (e.g., the processor 120 or the sensor module 176) of the electronic device 101. The various data may include, for example, software (e.g., the program 140) and input data or output data for a command related thereto. The memory 130 may include the volatile memory 132 or the non-volatile memory 134.

The program 140 may be stored in the memory 130 as software, and may include, for example, an operating system (OS) 142, middleware 144, or an application 146.

The input device 150 may receive a command or data to be used by other component (e.g., the processor 120) of the electronic device 101, from the outside (e.g., a user) of the electronic device 101. The input device 150 may include, for example, a microphone, a mouse, a keyboard, or a digital pen (e.g., a stylus pen).

The sound output device 155 may output sound signals to the outside of the electronic device 101. The sound output device 155 may include, for example, a speaker or a receiver. The speaker may be used for general purposes, such as playing multimedia or playing record, and the receiver may be used for an incoming calls. According to an embodiment, the receiver may be implemented as separate from, or as part of the speaker.

The display device 160 may visually provide information to the outside (e.g., a user) of the electronic device 101. The display device 160 may include, for example, a display, a hologram device, or a projector and control circuitry to control a corresponding one of the display, hologram device, and projector. According to an embodiment, the display device 160 may include touch circuitry adapted to detect a touch, or sensor circuitry (e.g., a pressure sensor) adapted to measure the intensity of force incurred by the touch.

The audio module 170 may convert a sound into an electrical signal and vice versa. According to an embodiment, the audio module 170 may obtain the sound via the input device 150, or output the sound via the sound output device 155 or a headphone of an external electronic device (e.g., an electronic device 102) directly (e.g., wiredly) or wirelessly coupled with the electronic device 101.

The sensor module 176 may detect an operational state (e.g., power or temperature) of the electronic device 101 or an environmental state (e.g., a state of a user) external to the electronic device 101, and then generate an electrical signal or data value corresponding to the detected state. According to an embodiment, the sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 177 may support one or more specified protocols to be used for the electronic device 101 to be coupled with the external electronic device (e.g., the electronic device 102) directly (e.g., wiredly) or wirelessly. According to an embodiment, the interface 177 may include, for example, a high definition multimedia interface (HDMI), a universal serial bus (USB) interface, a secure digital (SD) card interface, or an audio interface.

A connecting terminal 178 may include a connector via which the electronic device 101 may be physically connected with the external electronic device (e.g., the electronic device 102). According to an embodiment, the connecting terminal 178 may include, for example, a HDMI connector, a USB connector, a SD card connector, or an audio connector (e.g., a headphone connector).

The haptic module 179 may convert an electrical signal into a mechanical stimulus (e.g., a vibration or a movement) or electrical stimulus which may be recognized by a user via his tactile sensation or kinesthetic sensation. According to an embodiment, the haptic module 179 may include, for example, a motor, a piezoelectric element, or an electric stimulator.

The camera module 180 may capture a still image or moving images. According to an embodiment, the camera module 180 may include one or more lenses, image sensors, image signal processors, or flashes.

The power management module 188 may manage power supplied to the electronic device 101. According to one embodiment, the power management module 188 may be implemented as at least part of, for example, a power management integrated circuit (PMIC).

The battery 189 may supply power to at least one component of the electronic device 101. According to an embodiment, the battery 189 may include, for example, a primary cell which is not rechargeable, a secondary cell which is rechargeable, or a fuel cell.

The communication module 190 may support establishing a direct (e.g., wired) communication channel or a wireless communication channel between the electronic device 101 and the external electronic device (e.g., the electronic device 102, the electronic device 104, or the server 108) and performing communication via the established communication channel. The communication module 190 may include one or more communication processors that are operable independently from the processor 120 (e.g., the application processor (AP)) and supports a direct (e.g., wired) communication or a wireless communication. According to an embodiment, the communication module 190 may include a wireless communication module 192 (e.g., a cellular communication module, a short-range wireless communication module, or a global navigation satellite system (GNSS) communication module) or a wired communication module 194 (e.g., a local area network (LAN) communication module or a power line communication (PLC) module). A corresponding one of these communication modules may communicate with the external electronic device via the first network 198 (e.g., a short-range communication network, such as Bluetooth™, wireless-fidelity (Wi-Fi) direct, or infrared data association (IrDA)) or the second network 199 (e.g., a long-range communication network, such as a cellular network, the Internet, or a computer network (e.g., LAN or wide area network (WAN)). These various types of communication modules may be implemented as a single component (e.g., a single chip), or may be implemented as multi components (e.g., multi chips) separate from each other. The wireless communication module 192 may identify and authenticate the electronic device 101 in a communication network, such as the first network 198 or the second network 199, using subscriber information (e.g., international mobile subscriber identity (IMSI)) stored in the subscriber identification module 196.

The antenna module 197 may transmit or receive a signal or power to or from the outside (e.g., the external electronic device) of the electronic device 101. According to an embodiment, the antenna module 197 may include an antenna including a radiating element composed of a conductive material or a conductive pattern formed in or on a substrate (e.g., PCB). According to an embodiment, the antenna module 197 may include a plurality of antennas. In such a case, at least one antenna appropriate for a communication scheme used in the communication network, such as the first network 198 or the second network 199, may be selected, for example, by the communication module 190 (e.g., the wireless communication module 192) from the plurality of antennas. The signal or the power may then be transmitted or received between the communication module 190 and the external electronic device via the selected at least one antenna. According to an embodiment, another component (e.g., a radio frequency integrated circuit (RFIC)) other than the radiating element may be additionally formed as part of the antenna module 197.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 101 and the external electronic device 104 via the server 108 coupled with the second network 199. Each of the electronic devices 102 and 104 may be a device of a same type as, or a different type, from the electronic device 101. According to an embodiment, all or some of operations to be executed at the electronic device 101 may be executed at one or more of the external electronic devices 102, 104, or 108. For example, if the electronic device 101 should perform a function or a service automatically, or in response to a request from a user or another device, the electronic device 101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 101. The electronic device 101 may provide the outcome, with or without further processing of the outcome, as at least part of a reply to the request. To that end, a cloud computing, distributed computing, or client-server computing technology may be used, for example.

The electronic device according to various embodiments may be one of various types of electronic devices. The electronic devices may include, for example, a portable communication device (e.g., a smartphone), a computer device, a portable multimedia device, a portable medical device, a camera, a wearable device, or a home appliance. According to an embodiment of the disclosure, the electronic devices are not limited to those described above.

It should be appreciated that various embodiments of the present disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C." may include any one of, or all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), it means that the element may be coupled with the other element directly (e.g., wiredly), wirelessly, or via a third element.

As used herein, the term "module" may include a unit implemented in hardware, software, or firmware, and may interchangeably be used with other terms, for example. "logic," "logic block," "part," or "circuitry". A module may be a single integral component, or a minimum unit or part thereof, adapted to perform one or more functions. For example, according to an embodiment, the module may be implemented in a form of an application-specific integrated circuit (ASIC).

Various embodiments as set forth herein may be implemented as software (e.g., the program 140) including one or more instructions that are stored in a storage medium (e.g., internal memory 136 or external memory 138) that is readable by a machine (e.g., the electronic device 101). For example, a processor(e.g., the processor 120) of the machine (e.g., the electronic device 101) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a complier or a code executable by an interpreter. The machine-readable storage medium may be provided in the form of a non-transitory storage medium. Wherein, the term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to an embodiment, a method according to various embodiments of the disclosure may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloaded or uploaded) online via an application store (e.g., PlayStore™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to various embodiments, each component (e.g., a module or a program) of the above-described components may include a single entity or multiple entities. According to various embodiments, one or more of the above-described components may be omitted, or one or more other components may be added. Alternatively or additionally, a plurality of components (e.g., modules or programs) may be integrated into a single component. In such a case, according to various embodiments, the integrated component may still perform one or more functions of each of the plurality of components in the same or similar manner as they are performed by a corresponding one of the plurality of components before the integration. According to various embodiments, operations performed by the module, the program, or another component may be carried out sequentially, in parallel, repeatedly, or heuristically, or one or more of the operations may be executed in a different order or omitted, or one or more other operations may be added.

Figure 2:
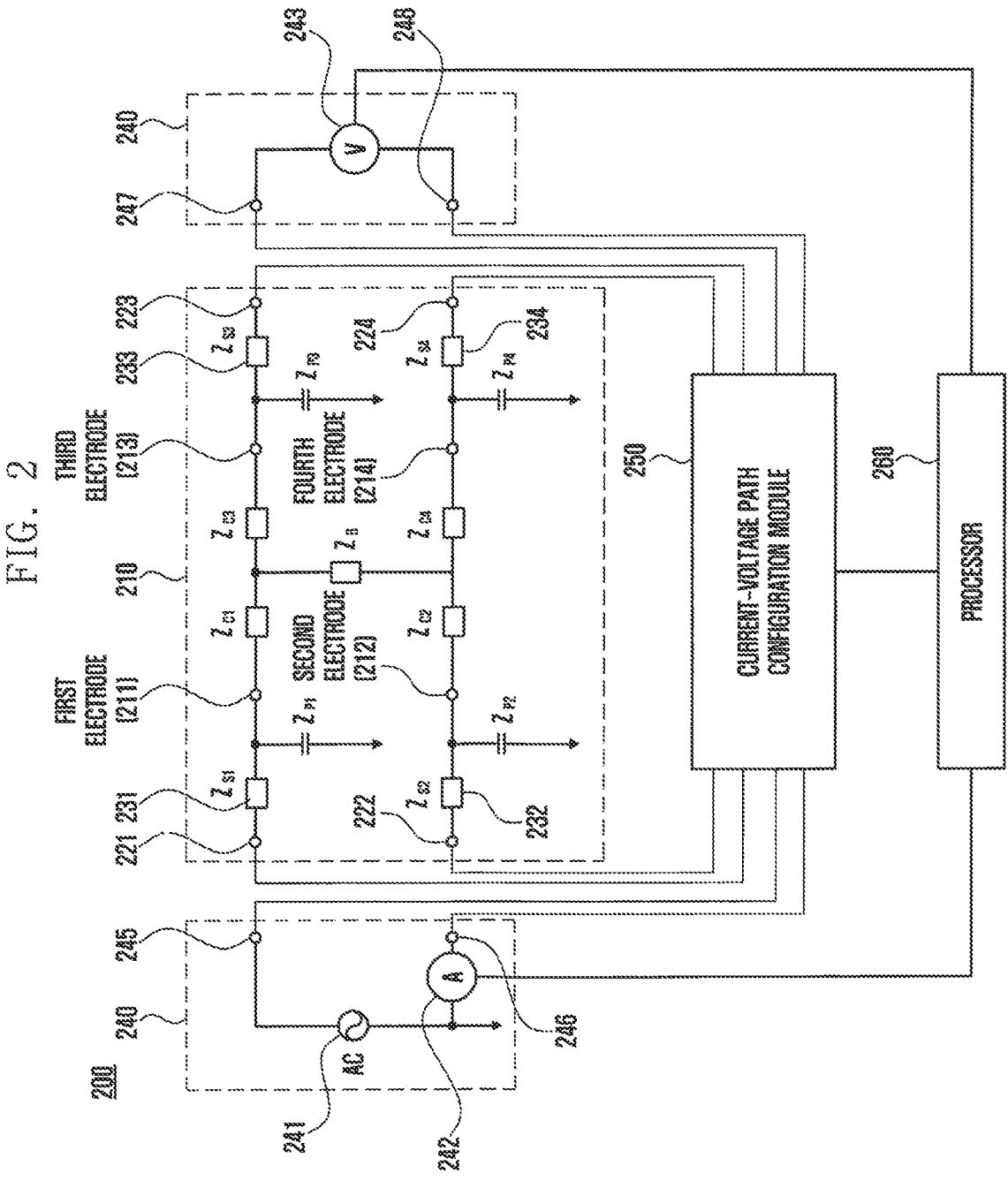
FIG. 2 illustrates an electronic device configured to correct an error in values of bio-impedance caused by leakage of an electrical signal due to a parasitic component according to various embodiments of the disclosure.

FIG. 2 illustrates an electronic device 200 configured to correct an error in values of bio-impedance caused by leakage of an electrical signal due to a parasitic component according to various embodiments of the disclosure. Referring to FIG. 2, the electronic device 200 (e.g., the electronic device 101 of FIG. 1) includes a bio-contact circuit 210, a current-voltage measurement module 240, a current-voltage path configuration module 250, and a processor 260 (e.g., the processor 120 of FIG. 1). At least one of the bio-contact circuit 210, the current-voltage measurement module 240, or the current-voltage path configuration module 250 may be an element (e.g., a biometric sensor) included in the sensor module 176 of FIG. 1.

According to various embodiments, the bio-contact circuit 210 may include four electrodes 211, 212, 213, and 214, four ports 221, 222, 223, and 224, and four circuit elements 231, 232, 233, and 234.

The electrodes 211, 212, 213, and 214 are disposed on the surface of the electronic device 200 so as to come in contact with a biological body, and thus may be electrically connected to each other through the biological body. The first electrode 211 may be electrically connected to the first port 221 through the first circuit element 231. The second electrode 212 may be electrically connected to the second port 222 through the second circuit element 232. The third electrode 213 may be electrically connected to the third port 223 through the third circuit element 233. The fourth electrode 214 may be electrically connected to the fourth port 224 through the fourth circuit element 234.

Each of the circuit elements 231, 232, 233, and 234 may include electronic components (e.g., capacitors and resistors) for removing a direct current component from an electrical signal flowing from a corresponding port to a corresponding electrode (or vice versa). The circuit elements 231, 232, 233, and 234 may each have ZS1, ZS2, ZS3, and ZS4 as impedance components given during circuit design, and these impedance components may be referred to as characteristic impedances. Impedance components ZC1, ZC2, ZC3, and ZC4 may be generated between the biological body and the electrodes 211, 212, 213, and 214, respectively, and may be referred to as contact impedances. The contact impedances may change according to the surface condition (skin condition) of the biological body. The contact impedance may also change depending on the frequency of an applied electrical signal. An impedance component ZB existing between the contact impedances is a component to be acquired, and ZB may be referred to as a bio-impedance. Impedance components ZP1, ZP2, ZP3, and ZP4, which are not intended during circuit design, may be parasitic between the electrodes 211, 212, 213, 214 and the ground (for example, the ground of the electronic device 200), respectively (References 1 to 5), and the impedance components may be referred to as parasitic impedances. Electrical signals (e.g., current and/or voltage) may leak from the bio-contact circuit 210 toward the ground due to parasitic components, and as a result, an error in the bio-impedance to be acquired may occur due to the leakage of the electrical signal. The value of the parasitic impedance may be obtained through an impedance analysis device.

Reference 1: Brian A. Mazzeo, "Parasitic capacitance influence of potential-sensing electrodes on four-electrode liquid impedance measurements", Journal of Applied Physics 105, 09410 (2009)

Reference 2: Brian. A. Mazzeo, and Andrew J. Flewitt, "Two- and four-electrode, wide-bandwidth, dielectric spectrometer for conductive liquids: Theory, limitations, and experiment". Journal of Applied Physics 102, 104106 (2007)

Reference 3: Damjan Pelc. Sanjin Marion, and Mario Basletic. "Four-contact impedance spectroscopy of conductive liquid samples", Review of Scientific Instruments 82, 073907 (2011)

Reference 4: Sverre Grimnes and Ørjan G Martinsen, "Sources of error in tetrapolar impedance measurements on biomaterials and other ionic conductors", Journal of Physics D: Applied Physics, vol. 40, no. 1 (2007)

Reference 5: S. Brigati, G. Caiulo, F. Maloberti, and G. Torelli, "Active Compensation of Parasitic Capacitances for Very High Frequency CMOS DACs", IEEE International Symposium on Circuits and Systems (1993)

According to various embodiments, the current-voltage measurement module 240 may include a feeding port 245, a current measurement port 246, a first voltage measurement port 247, a second voltage measurement port 248, an AC signal generator 241, an ammeter 242, and a voltmeter 243.

The feeding port 245 and the current measurement port 246 may be electrically connected to the bio-contact circuit 210 through the current-voltage path configuration module 250.

The AC signal generator 241 may generate an electrical signal and may apply the electrical signal to the bio-contact circuit 210 through the feeding port 245.

The ammeter 242 may receive an electrical signal from the bio-contact circuit 210 through the current measurement port 246, measure the current of the received electrical signal, and transmit the current measurement value to the processor 260.

The first voltage measurement port 247 and the second voltage measurement port 248 may be electrically connected to the bio-contact circuit 210 through the current-voltage path configuration module 250.

The voltmeter 243 may measure a voltage between the first voltage measurement port 247 and the second voltage measurement port 248, and may transmit the voltage measurement value to the processor 260.

According to various embodiments, the current-voltage path configuration module (hereinafter, the path configuration module) 250 may electrically connect the ports 221, 222, 223, and 224 of the bio-contact circuit 210 to the current-voltage measurement module 240 under the control of the processor 260.

According to various embodiments, the processor 260 may control the path configuration module 250 to configure a current path established from one of the electrodes 211, 212, 213, 214 to another electrode. The processor 260 may control the path configuration module 250 to configure a voltage path established from one of the electrodes 211, 212, 213, and 214 to another electrode.

The processor 260 may control the path configuration module 250 to configure the voltage path such that one of the two electrodes of the voltage path matches with one of the two electrodes of the current path, the other one of the two electrodes of the voltage path is different from the other one of the two electrodes of the current path, and no bio-impedance ZB is included on the voltage path. For example, the processor 260 may configure a current-voltage path in the bio-contact circuit 210 such that the first electrode 211 is included on the current path and the voltage path and no bio-impedance ZB is included in the voltage path.

The processor 260 may receive, from the ammeter 242 or the voltmeter 243, a current or voltage value measured in a state in which the current-voltage path constitutes the bio-contact circuit 210. The processor 260 may measure the impedance of the first electrode 211 (including an error caused by the parasitic impedance ZP1 between the first electrode 211 and the ground) on the current/voltage path, by using the received current/voltage values. The processor 260 may measure the impedances of the remaining electrodes 212, 213, and 214 in the same manner as described above.

According to an embodiment, the processor 260 may transmit a first control signal (e.g., bio-impedance inclusion OFF, polarity swapping OFF, and current-voltage swapping OFF) to the path configuration module 250 in order to measure the contact impedance of the second electrode 212. For example, in the case of "bio-impedance inclusion OFF", the bio-impedance ZB may not be included in the voltage path. When the polarity swapping signal changes from an OFF state to an ON state, a start electrode and an end electrode may be switched in the current path. For example, in a state in which a current path is established from the first electrode 211 to the second electrode 212, if the polarity swapping signal is changed from an OFF state to an ON state, the current path may be switched to a current path established from the second electrode 212 to the first electrode 211. When the current-voltage swapping signal is changed from an OFF state to an ON state, the start electrode and end electrode may be switched in the voltage path. For example, in a state in which the voltage path is established from the fourth electrode 214 to the second electrode 212, if the current-voltage swapping signal is changed from an OFF state to an ON state, the voltage path may be switched to a voltage path established from the second electrode 212 to the fourth electrode 214. Paths established according to various combinations of bio-impedance inclusion ON/OFF, polarity swapping ON/OFF, and current-voltage swapping ON/OFF may be summarized as shown in Table 1 below.

The path configuration module 250 may connect the first port 221 to the feeding port 245 and connect the second port 222 to the current measurement port 246 in response to the first control signal. Accordingly, a first current path established from the first electrode 211 to the second electrode 212 may be formed in the bio-contact circuit 210. The path configuration module 250 may connect the fourth port 224 to the first voltage measurement port 247 and connect the second port 222 to the second voltage measurement port 248 in response to the first control signal. Accordingly, a first voltage path established from the fourth electrode 214 to the second electrode 212 may be formed in the bio-contact circuit 210. The processor 260 may receive, from an ammeter 242 and a voltmeter 243, current/voltage values measured in a state in which a first current-voltage path including the first current path and the first voltage path constitutes the bio-contact circuit 210. The processor 260 may measure the impedance of the second electrode 212 (including an error caused by the parasitic impedance ZP2 between the second electrode 212 and the ground), by using the received current/voltage values.

The processor 260 may change the current-voltage path in order to measure the contact impedance of the fourth electrode 214. For example, the processor 260 may transmit a second control signal (e.g., bio-impedance inclusion OFF, polarity swapping OFF, and current-voltage swapping ON) to the path configuration module 250. The path configuration module 250 may connect the third port 223 to the feeding port 245, connect the fourth port 224 to the current measurement port 246, and connect the second port 222 to the first voltage measurement port 247, and connect the fourth port 224 to the second voltage measurement port 248 in response to the second control signal. Accordingly, a second current-voltage path, which includes a second current path established from the third electrode 213 to the fourth electrode 214 and a second voltage path established from the second electrode 212 to the fourth electrode 214, may be formed in the bio-contact circuit 210. The processor 260 may receive the measured current/voltage values from the ammeter 242 and the voltmeter 243 in a state in which a second current-voltage path constitutes the bio-contact circuit 210. The processor 260 may measure the impedance of the fourth electrode 214 (including an error caused by the parasitic impedance ZP4 between the fourth electrode 214 and the ground), by using the received current/voltage values.

The processor 260 may change the polarity of the current in order to measure the contact impedance of the first electrode 211. For example, the processor 260 may transmit a third control signal (e.g., bio-impedance inclusion OFF, polarity swapping ON, and current-voltage swapping OFF) to the path configuration module 250. The path configuration module 250 may connect the second port 222 to the feeding port 245, connect the first port 221 to the current measurement port 246, and connect the third port 223 to the first voltage measurement port 247, and connect the first port 221 to the second voltage measurement port 248 in response to the third control signal. Accordingly, a third current-voltage path, which includes a third current path established from the second electrode 212 to the first electrode 211 and a third voltage path established from the third electrode 213 to the first electrode 211, may be formed in the bio-contact circuit 210. The processor 260 may receive, from the ammeter 242 and the voltmeter 243, the current/voltage values measured in a state in which a third current-voltage path constitutes the bio-contact circuit 210. The processor 260 may measure the impedance of the first electrode 211 (including an error caused by the parasitic impedance ZP1 between the first electrode 211 and the ground) by using the received current/voltage values.

The processor 260 may change a current polarity and a current-voltage path in order to measure the contact impedance of the third electrode 213. For example, the processor 260 may transmit a fourth control signal (e.g., bio-impedance inclusion OFF, polarity swapping ON, and current-voltage swapping ON) to the path configuration module 250. In response to the fourth control signal, the processor 260 may connect the fourth port 224 to the feeding port 245, connect the third port 223 to the current measurement port 246, connect the first port 221 to the first voltage measurement port 247, and connect the third port 223 to the second voltage measurement port 248. Accordingly, a fourth current-voltage path, which includes a fourth current path established from the fourth electrode 214 to the third electrode 213 and a fourth voltage path established from the first electrode 211 to the third electrode 213, may be formed in the bio-contact circuit 210. The processor 260 may receive, from the ammeter 242 and the voltmeter 243, the current/voltage values measured in a state in which a fourth current-voltage path constitutes the bio-contact circuit 210. The processor 260 may measure the impedance of the third electrode 213 (including an error caused by the parasitic impedance ZP3 between the third electrode 213 and the ground), by using the received current/voltage values.

According to various embodiments, the processor 260 may correct the impedance measurement value, by using the parasitic impedances ZP1, ZP2, ZP3, and ZP4 and the characteristic impedances ZS1, ZS2, ZS3, and ZS4 (e.g., remove an error caused by the parasitic impedance from the measured value), so as to obtain contact impedances ZC1, ZC2, ZC3, and ZC4.

According to various embodiments, the processor 260 may control the path configuration module 250 to configure a current path and a voltage path such that one of the two electrodes of the voltage path matches with one of the two electrodes of the current path, the other one of the two electrodes of the voltage path is different from the other one of the two electrodes of the current path, and the bio-impedance ZB is included in both the current path and the voltage path. The processor 260 may receive, from the ammeter 242 and the voltmeter 243, the current/voltage values measured in a state in which the current-voltage path constitutes the bio-contact circuit 210. The processor 260 may calculate the bio-impedance ZB by using the received current/voltage values, characteristic impedances ZS1, ZS2, ZS3, and ZS4, parasitic impedances ZP1, ZP2, ZP3, and ZP4, and contact impedances ZC1, ZC2, ZC3, and ZC4.

According to an embodiment, the processor 260 may configure a current-voltage path in the bio-contact circuit 210 such that the second electrode 212 and the bio-impedance ZB are included in the current path and the voltage path. For example, the processor 260 may transmit a fifth control signal (e.g., bio-impedance inclusion ON, polarity swapping OFF, and current-voltage swapping OFF) to the path configuration module 250. In response to the fifth control signal, the path configuration module 250 may connect the first port 221 to the feeding port 245, connect the second port 222 to the current measurement port 246, connect the third port 223 to the first voltage measurement port 247, and connect the second port 222 to the second voltage measurement port 248. Accordingly, a fifth current-voltage path, which includes a first current path established from the first electrode 211 to the second electrode 212 and a fifth voltage path established from the third electrode 213 to the second electrode 212, may be formed in the bio-contact circuit 210. The processor 260 may receive, from the ammeter 242 and the voltmeter 243, the current/voltage values measured in a state in which a fifth current-voltage path constitutes the bio-contact circuit 210. The processor 260 may calculate a first bio-impedance ZB1 by using the current/voltage values, the characteristic impedance value, the parasitic impedance value, and the contact impedance value, which are measured through the fifth current-voltage path.

According to an embodiment, the processor 260 may change a current-voltage path such that the fourth electrode 214 and the bio-impedance ZB are included in a current path and a voltage path. For example, the processor 260 may transmit a sixth control signal (e.g., bio-impedance inclusion ON, polarity swapping OFF, and current-voltage swapping ON) to the path configuration module 250. The path configuration module 250 may control, in response to the sixth control signal, the path configuration module 250 to connect the third port 223 to the feeding port 245, connect the fourth port 224 to the current measurement port 246, connect the first port 221 to the first voltage measurement port 247, and connect the fourth port 224 to the second voltage measurement port 248. Accordingly, a sixth current-voltage path, which includes a second current path established from the third electrode 213 to the fourth electrode 214 and a sixth voltage path established from the first electrode 211 to the fourth electrode 214, may be formed in the bio-contact circuit 210. The processor 260 may receive, from the ammeter 242 and the voltmeter 243, the current/voltage values measured in a state in which the sixth current-voltage path constitutes the bio-contact circuit 210. The processor 260 may calculate a second bio-impedance ZB2 by using the current/voltage values, the characteristic impedance value, the parasitic impedance value, and the contact impedance value, which are measured through the sixth current-voltage path.

According to an embodiment, the processor 260 may change a current polarity such that the first electrode 211 and the bio-impedance ZB are included in the current path and the voltage path. For example, the processor 260 may transmit a seventh control signal (e.g., bio-impedance inclusion ON, polarity swapping ON, and current-voltage swapping OFF) to the path configuration module 250. The path configuration module 250 may control, in response to the seventh control signal, the path configuration module 250 to connect the second port 222 to the feeding port 245, connect the first port 221 to the current measurement port 246, connect the fourth port 224 to the first voltage measurement port 247, and connect the first port 221 to the second voltage measurement port 248. Accordingly, a seventh current-voltage path, which includes a third current path established from the second electrode 212 to the first electrode 211 and a seventh voltage path established from the fourth electrode 214 to the first electrode 211, may be formed in the bio-contact circuit 210. The processor 260 may receive, from the ammeter 242 and the voltmeter 243, the current/voltage values measured in a state in which the seventh current-voltage path constitutes the bio-contact circuit 210. The processor 260 may calculate a third bio-impedance ZB3 by using the current/voltage values, the characteristic impedance value, the parasitic impedance value, and the contact impedance value, which are measured through the seventh current-voltage path.

According to an embodiment, the processor 260 may change a current polarity and a current-voltage path such that the third electrode 213 and the bio-impedance ZB are included in a current path and a voltage path. For example, the processor 260 may transmit an eighth control signal (e.g., bio-impedance inclusion ON, polarity swapping ON, and current-voltage swapping ON) to the path configuration module 250. In response to the eighth control signal, the path configuration module 250 may connect the fourth port 224 to the feeding port 245, connect the third port 223 to the current measurement port 246, connect the second port 222 to the first voltage measurement port 247, and connect the third port 223 to the second voltage measurement port 248. Accordingly, an eighth current-voltage path, which includes a fourth current path established from the fourth electrode 214 to the third electrode 213 and an eighth voltage path established from the second electrode 212 to the third electrode 213, may be formed in the bio-contact circuit 210. The processor 260 may receive, from the ammeter 242 and the voltmeter 243, the current/voltage values measured in a state in which the eighth current-voltage path constitutes the bio-contact circuit 210. The processor 260 may calculate a fourth bio-impedance ZB4 by using the current/voltage values, the characteristic impedance value, the parasitic impedance value, and the contact impedance value, which are measured through the eighth current-voltage path.

The first to the eighth current-voltage path that may be configured in the bio-contact circuit 210 as described above may be summarized in Table 1 as follows.

TABLE 1

| | Control signal | | | Path of bio-contact circuit | | |
| No. | Bio-impedance $(Z_B)$ inclusion | Polarity swapping | Current-voltage swapping | Current path | Voltage path | Selected impedance |
|---|---|---|---|---|---|---|
| 1 | OFF | OFF | OFF | Electrode 1 to electrode 2 | Electrode 4 to electrode 2 | $Z_{C2}$ |

TABLE 1-continued

| | Control signal | | | Path of bio-contact circuit | | |
|---|---|---|---|---|---|---|
| No. | Bio-impedance ($Z_B$) inclusion | Polarity swapping | Current-voltage swapping | Current path | Voltage path | Selected impedance |
| 2 | OFF | OFF | ON | Electrode 3 to electrode 4 | Electrode 2 to electrode 4 | $Z_{C4}$ |
| 3 | OFF | ON | OFF | Electrode 2 to electrode 1 | Electrode 3 to electrode 1 | $Z_{C1}$ |
| 4 | OFF | ON | ON | Electrode 4 to electrode 3 | Electrode 1 to electrode 3 | $Z_{C3}$ |
| 5 | ON | OFF | OFF | Electrode 1 to electrode 2 | Electrode 3 to electrode 2 | $Z_{C2}, Z_B$ |
| 6 | ON | OFF | ON | Electrode 3 to electrode 4 | Electrode 1 to electrode 4 | $Z_{C4}, Z_B$ |
| 7 | ON | ON | OFF | Electrode 2 to electrode 1 | Electrode 4 to electrode 1 | $Z_{C1}, Z_B$ |
| 8 | ON | ON | ON | Electrode 4 to electrode 3 | Electrode 2 to electrode 3 | $Z_{C3}, Z_B$ |

Figure 3:
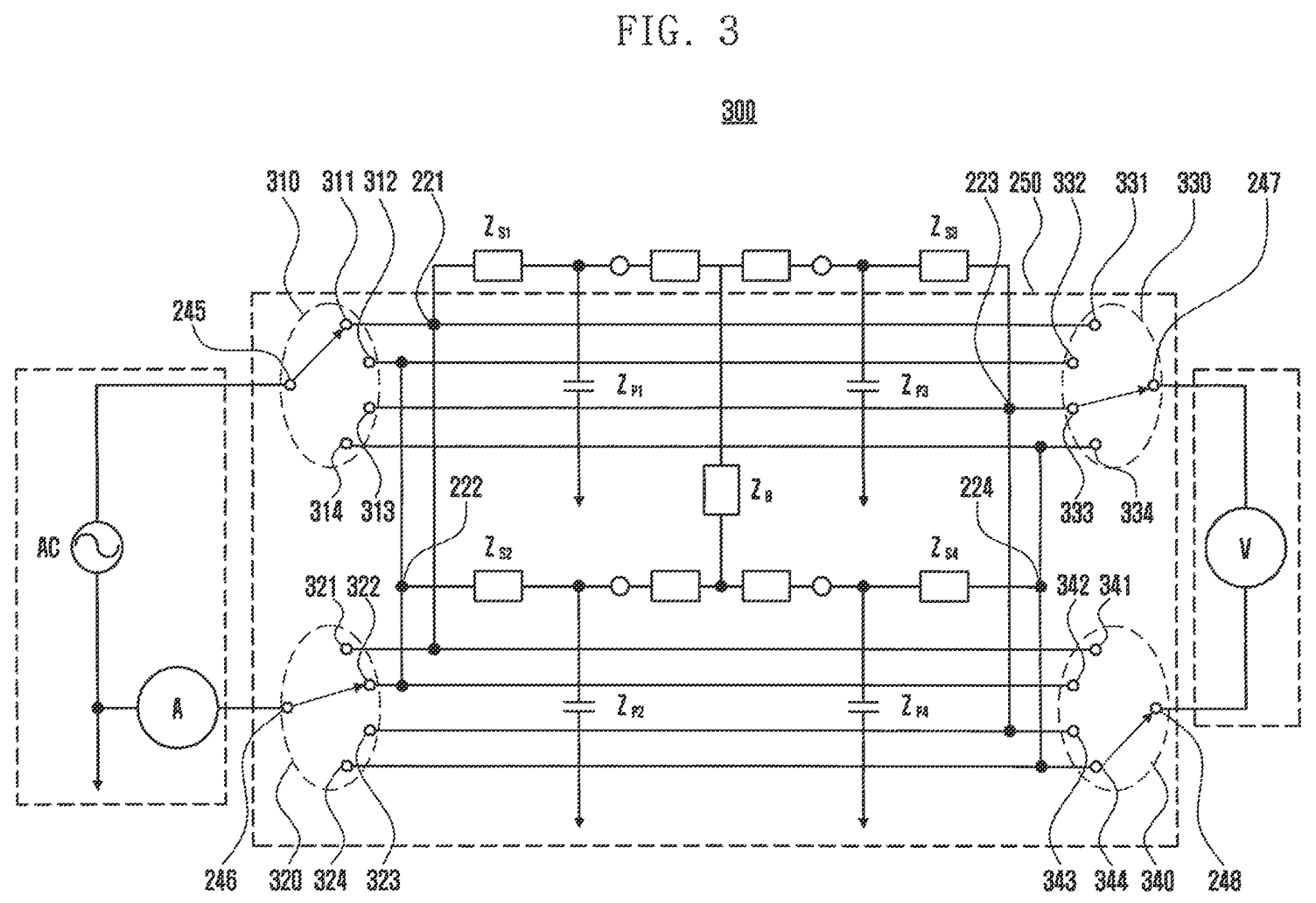

FIG. 3 is a circuit diagram 300 of a path configuration module 250 according to various embodiments of the disclosure. Referring to FIG. 3, the path configuration module 250 may include four switches 310, 320, 330, and 340 each having four terminals.

A 1-1 terminal 311, a 1-2 terminal 312, a 1-3 terminal 313, and a 1-4 terminal 314 of the first switch 310 may be electrically connected to the first port 221, the second port 222, the third port 223, and the fourth port 224 of the bio-contact circuit 210, respectively, and the first switch 310 may connect the feeding port 245 to one of the four terminals 311, 312, 313, and 314 under the control of the processor 260.

A 2-1 terminal 321, a 2-2 terminal 322, a 2-3 terminal 323, and a 2-4 terminal 324 of the second switch 320 may be electrically connected to the first port 221, the second port 222, the third port 223, and the fourth port 224 of the bio-contact circuit 210, respectively, and the second switch 320 may connect the current measurement port 246 to one of the four terminals 321, 322, 323, and 324 under the control of the processor 260.

A 3-1 terminal 331, a 3-2 terminal 332, a 3-3 terminal 333, and a 3-4 terminal 334 of the third switch 330 may be connected to the first port 221, the second port 222, the third port 223, and the fourth port 224 of the bio-contact circuit 210, respectively, and the third switch 330 may connect the first voltage measurement port 247 to one of the four terminals 331, 332, 333, and 334 under the control of the processor 260.

A 4-1 terminal 341, a 4-2 terminal 342, a 4-3 terminal 343, and a 4-4 terminal 344 of the fourth switch 340 may be connected to the first port 221, the second port 222, the third port 223, and the fourth port 224 of the bio-contact circuit 210, respectively, and the third switch 330 may connect the second voltage measurement port 248 to one of the four terminals 341, 342, 343, and 344 under the control of the processor 260.

Figure 4:
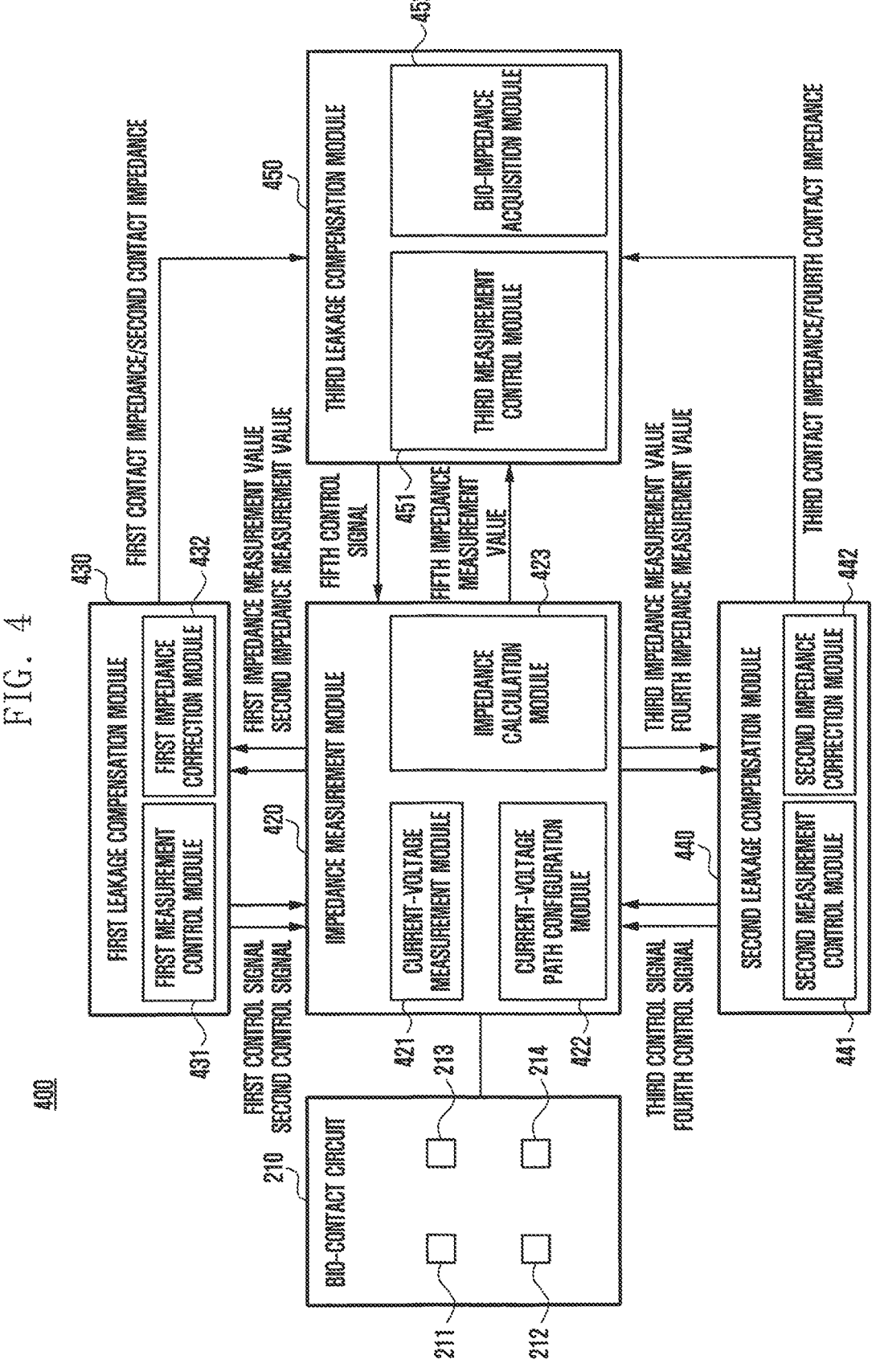
FIG. 4 illustrates an electronic device according to various embodiments of the disclosure.

FIG. 4 illustrates an electronic device 400 according to various embodiments of the disclosure. Referring to FIG. 4, the electronic device 400 (e.g., the electronic device 200 of FIG. 2) may include a bio-contact circuit 210 of FIG. 2, an impedance measurement module 420, a first leakage compensation module 430, a second leakage compensation module 440, and a third leakage compensation module 450.

According to various embodiments, the impedance measurement module 420 may include a current-voltage measurement module 421 (e.g., the current-voltage measurement module 240 of FIG. 2), and a path configuration module 422 (e.g., the path configuration module 250 of FIG. 2) and an impedance calculation module 423 (e.g., the processor 260 of FIG. 2). The path configuration module 422 may configure, based on a control signal (e.g., one of the control signals in Table 1) received from one of the leakage compensation modules 430, 440, and 450, a current-voltage path of the bio-contact circuit 210 (e.g., a current-voltage path corresponding to the received control signal in Table 1). The current-voltage measurement module 240 may measure the current and voltage of the bio-contact circuit 210 in a state in which the current-voltage path constitutes the bio-contact circuit. The impedance calculation module 423 may calculate impedance by using the measured current/voltage value, and may transmit the impedance measurement value to the leakage compensation module that has transmitted the control signal.

According to various embodiments, the first leakage compensation module 430 (e.g., the processor 260 of FIG. 2) may include a first measurement control module 431 and a first impedance correction module 432. The first measurement control module 431 may output a first control signal (e.g., the first control signal in Table 1) for acquisition of a contact impedance of the second electrode 212 to the impedance measurement module 420, and may receive, in response to the first control signal, a first impedance measurement value from the impedance measurement module 420. The first measurement control module 431 may output a second control signal (e.g., the second control signal in Table 1) for acquisition of a value of the contact impedance of the fourth electrode 214 to the impedance measurement module 420, and may receive, in response to the second control signal, a second impedance measurement value from the impedance measurement module 420. The first impedance correction module 432 may correct the first impedance measurement value and the second impedance measurement value, by using "the first impedance measurement value, the second impedance measurement value, a value of predetermined characteristic impedance (e.g., a characteristic impedance of a circuit element electrically connected to the second electrode 212, and a characteristic impedance of a circuit element electrically connected to the fourth electrode 214), and a value of a predetermined parasitic impedance (e.g., a parasitic impedance between the second electrode 212 and the ground, and a parasitic impedance between the fourth electrode 214 and the ground)". The first impedance correction module 432 may transfer the correction values (first contact impedance and second contact impedance) to the third leakage compensation module 450.

According to various embodiments, the second leakage compensation module 440 (e.g., the processor 260 of FIG. 2) may include a second measurement control module 441 and a second impedance correction module 442. The second measurement control module 441 may output a third control signal (e.g., the third control signal in Table 1) for acquisition of a value of a contact impedance of the first electrode 211 to the impedance measurement module 420, and may receive, in response to the third control signal, a third impedance measurement value from the impedance measurement module 420. The second measurement control module 441 may output a fourth control signal (e.g., the fourth control signal in Table 1) for acquisition of a value of a contact impedance of the third electrode 213 to the impedance measurement module 420, and may receive, in response to the fourth control signal, a fourth impedance measurement value from the impedance measurement module 420. The second impedance correction module 442 may correct the third impedance measurement value and the fourth impedance measurement value, by using "a third impedance measurement value, a fourth impedance measurement value, a value of a predetermined characteristic impedance (e.g., a characteristic impedance of a circuit element electrically connected to the first electrode 211, and a characteristic impedance of a circuit element electrically connected to the third electrode 213), and a value of a predetermined parasitic impedance (e.g., a parasitic impedance between the first electrode 211 and the ground, and a parasitic impedance between the third electrode 213 and the ground)". The first impedance correction module 432 may transfer the correction values (third contact impedance and fourth contact impedance) to the third leakage compensation module 450.

According to various embodiments, the third leakage compensation module 450 (e.g., the processor 260 of FIG. 2) may include a third measurement control module 451 and a bio-impedance acquisition module 452. The third measurement control module 451 may output a fifth control signal (e.g., one of the fifth to eighth control signals in Table 1) for acquisition of an impedance value of a biological body coming into contact with the bio-contact circuit 210 to the impedance measurement module 420, and may receive, in response to the fifth control signal, a fifth impedance measurement value from the impedance measurement module 420. The bio-impedance acquisition module 452 may calculate the bio-impedance by using "the fifth impedance measurement value, a predetermined parasitic impedance value, the calculated contact impedance value, and a predetermined characteristic impedance value". For example, in a case where a fifth current-voltage path, which includes a first current path established from the first electrode 211 to the second electrode 212 and a fifth voltage path established from the third electrode 213 to the second electrode 212, is formed in the bio-contact circuit 210 according to output of the fifth control signal of Table 1, the value of the bio-impedance may be obtained by using the contact impedances ZC2 and ZC3 of the electrodes 212 and 213 located on the fifth voltage path, the contact impedance ZC4 of the fourth electrode 214 that is not located on the fifth current-voltage path, the characteristic impedance ZS2 of a circuit element connected to an electrode commonly existing on the fifth voltage path and the fifth current path, the parasitic impedances ZP2 and ZP3 caused by a parasitic component existing between the electrodes 212 and 213 located on the fifth voltage path and the ground, and the parasitic impedance ZP4 caused by a parasitic component existing between the fourth electrode 214 that is not located on the fifth current-voltage path and the ground.

Figure 5A:
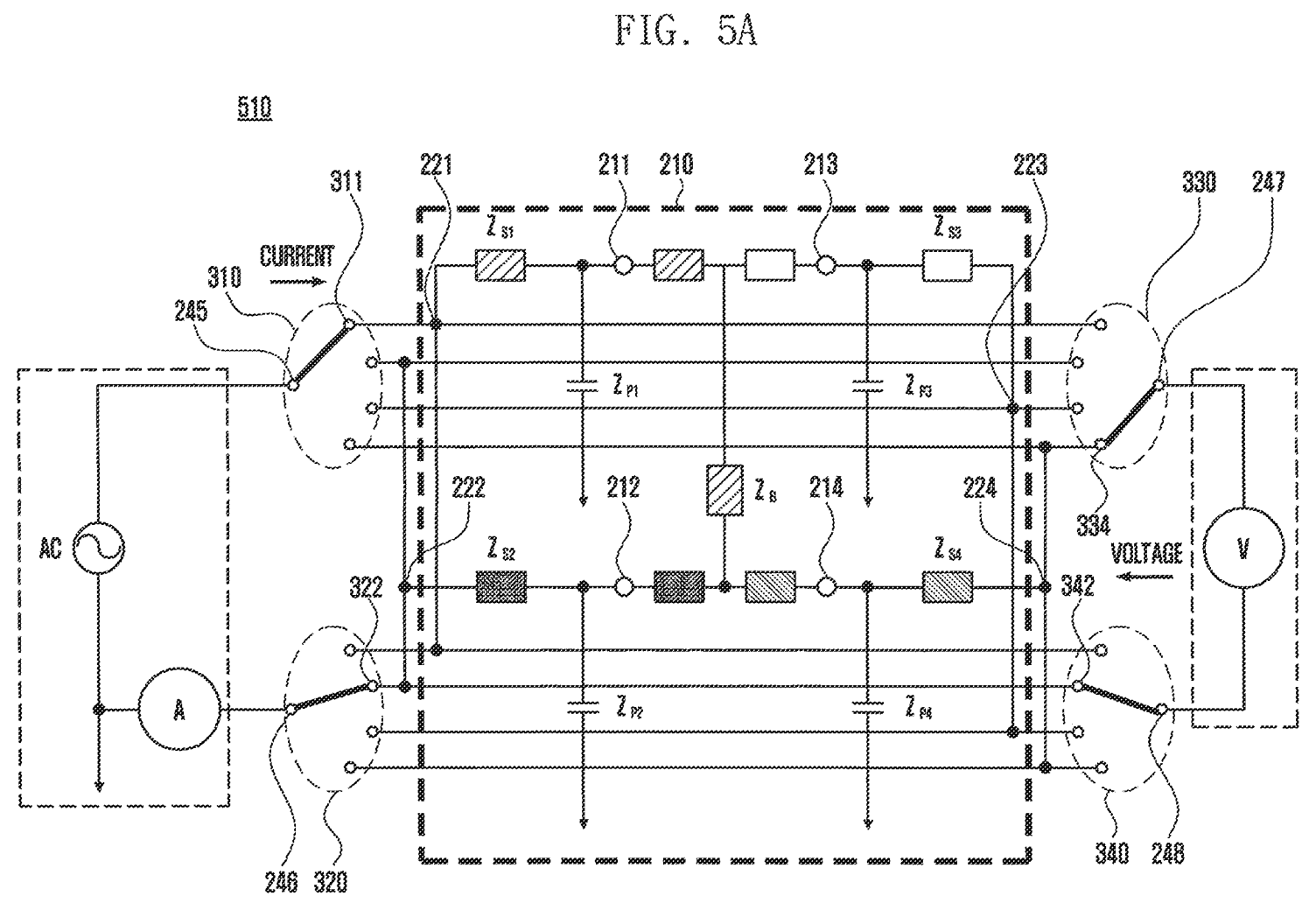
Figure 5B:
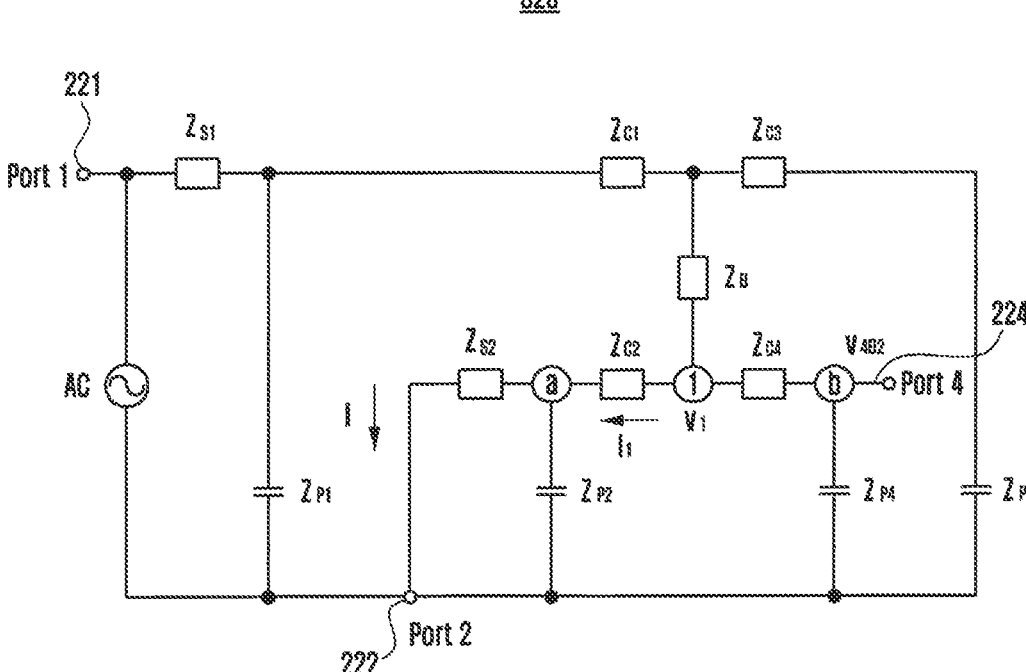
FIG. 5B illustrates an equivalent circuit corresponding to the current-voltage path of FIG. 5A.

FIG. 5A illustrates a current-voltage path 510 configured in the bio-contact circuit 210 according to the first control signal of Table 1, and FIG. 5B is an equivalent circuit 520 corresponding to the current-voltage path 510 of FIG. 5A.

Referring to FIG. 5A, in response to the first control signal of Table 1, the first switch 310 may connect the feed port 245 to the 1-1 terminal 311, the second switch 320 may connect the current measurement port 246 to the 2-2 terminal 322, the third switch 330 may connect the first voltage measurement port 247 to the 3-4 terminal 334, and the fourth switch 340 may connect the second voltage measurement port 248 to the 4-2 terminal 342. Accordingly, current i may flow from the first port 221 to the second port 222, and the voltage V4B2 may be measured in a direction going from the fourth port 224 to the second port 222.

Referring to FIG. 5B, a current may leak through the parasitic impedance ZP2 at node a, and a compensation value k11 for compensating for the current i may be expressed by Equation 1.

$$k_{11} \triangleq \frac{Z_{P2} + Z_{S2}}{Z_{P2}} \qquad \text{[Equation 1]}$$

Even at node b, a voltage may leak (e.g., a voltage drop) due to the influence of the parasitic component ZP3, and a compensated voltage value v1 at node 1 may be expressed as the right side of Equation 2. The voltage value v1 calculated using the impedances ZC2, ZS2, and ZP2 between node 1 and the second port 222 and the compensation value K11 may be expressed as the left side of Equation 2.

$$k_{11}i(Z_{C2} + Z_{S2}\|Z_{P2}) = \frac{Z_{C4} + Z_{P4}}{Z_{P4}}v_{4B2} \qquad \text{[Equation 2]}$$

Equation 2 includes the contact impedance ZC2 of the second electrode 212 to be obtained and the contact impedance ZC4 of the fourth electrode 214 to be obtained. That is, since ZC2 and ZC4 may not be obtained using Equation 2 alone, another Equation expressed by ZC2 and ZC4 is required. This equation can be obtained by changing the current-voltage path of the bio-contact circuit 210.

Figure 6A:
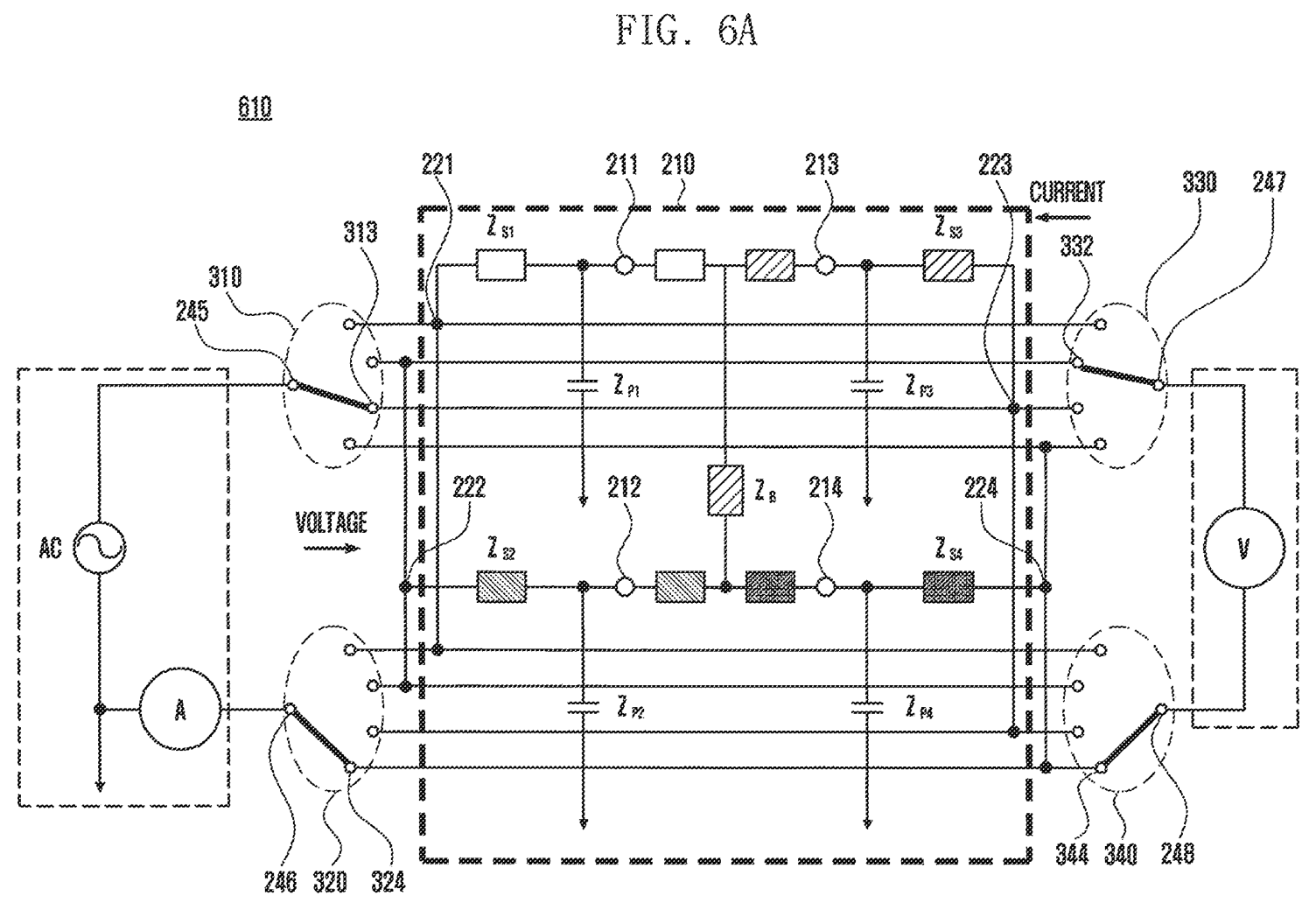
Figure 6B:
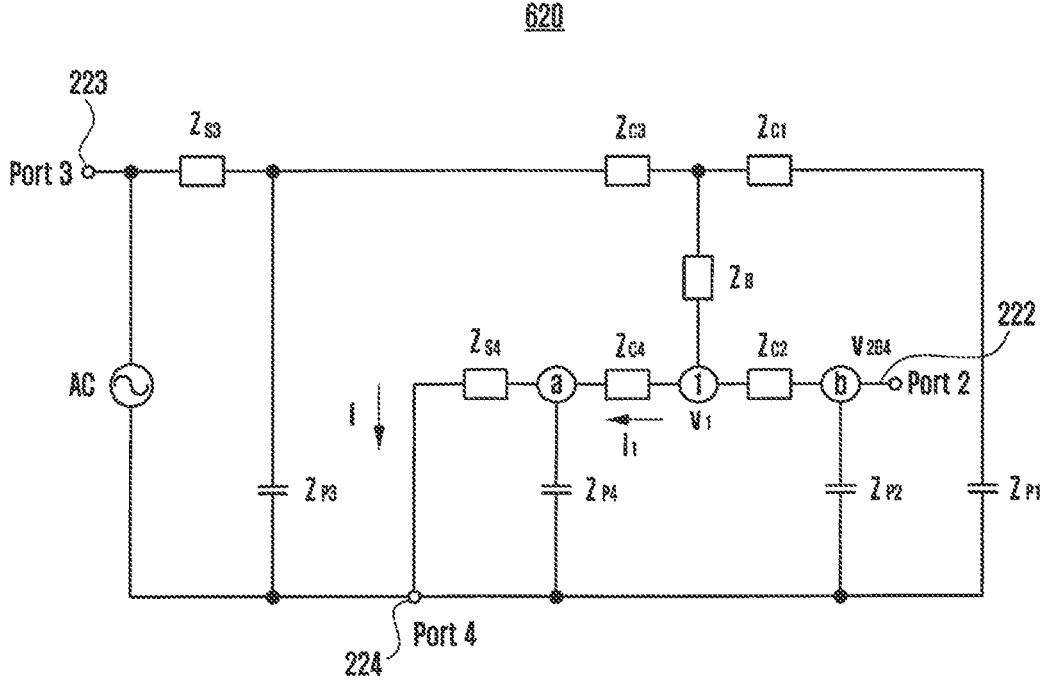
FIG. 6B illustrates an equivalent circuit corresponding to the current-voltage path of FIG. 6A.

FIG. 6A illustrates a current-voltage path 610 configured in the bio-contact circuit 210 according to the second control signal of Table 1, and FIG. 6B is an equivalent circuit 620 corresponding to the current-voltage path 610 of FIG. 6A.

Referring to FIG. 6A, in response to the second control signal, the first switch 310 may connect the feed port 245 to the 1-3 terminal 313, the second switch 320 may connect the current measurement port 246 to the 2-4 terminal 324, the third switch 330 may connect the first voltage measurement port 247 to the 3-2 terminal 332, and the fourth switch 340 may connect the second voltage measurement port 248 to the 4-4 terminal 344. Accordingly, current i may flow from the third port 223 to the fourth port 224, and the voltage V2B4 may be measured in a direction going from the second port 222 to the fourth port 224.

Referring to FIG. 6B, a current may leak through the parasitic impedance ZP4 at node a, and a compensation value k13 for compensating for the current i may be expressed by Equation 3.

$$k_{13} \overset{\Delta}{=} \frac{Z_{P4} + Z_{S4}}{Z_{P4}} \qquad \text{[Equation 3]}$$

Even at node b, a voltage may leak (e.g., a voltage drop) due to the influence of the parasitic component $Z_{P2}$, and a compensated voltage value v1 at node 1 may be expressed as the right side of Equation 4. The voltage value v1 calculated using the impedances $Z_{C4}$, $Z_{S4}$, and $Z_{P4}$ between node 1 and the fourth port 224 and the compensation value $K_{13}$ may be expressed as the left side of Equation 4.

$$k_{13}i(Z_{C4} + Z_{S4}\|Z_{P4}) = \frac{Z_{C2} + Z_{P2}}{Z_{P2}}v_{2B4} \qquad \text{[Equation 4]}$$

The processor (e.g., the processor 260 of FIG. 2 or the impedance calculation module 423 of FIG. 4) may obtain the first impedance measurement value $Z_{4B2}$ from the current value and voltage value $V_{4B2}$ measured through the current-voltage path 510 of FIG. 5A. The processor 260 may obtain a second impedance measurement value $Z_{2B4}$ from the current value and voltage value $V_{2B4}$ measured through the current-voltage path 610 of FIG. 6A.

The processor (e.g., the processor 260 of FIG. 2 or the first leakage compensation module 430 of FIG. 4) may obtain the contact impedance ZC2 of the second electrode 212 and the contact impedance ZC4 of the fourth electrode 214, by using Equation 5 expressed by combining Equation 2 with Equation 4.

$$\begin{bmatrix} Z_{C2} \\ Z_{C4} \end{bmatrix} = \begin{bmatrix} k_{11}Z_{P4} & -Z_{4B2} \\ -Z_{2B4} & k_{13}Z_{P2} \end{bmatrix}^{-1} \begin{bmatrix} Z_{P4}(Z_{4B2} - Z_{S2}) \\ Z_{P2}(Z_{2B4} - Z_{S4}) \end{bmatrix} \qquad \text{[Equation 5]}$$

Figure 7A:
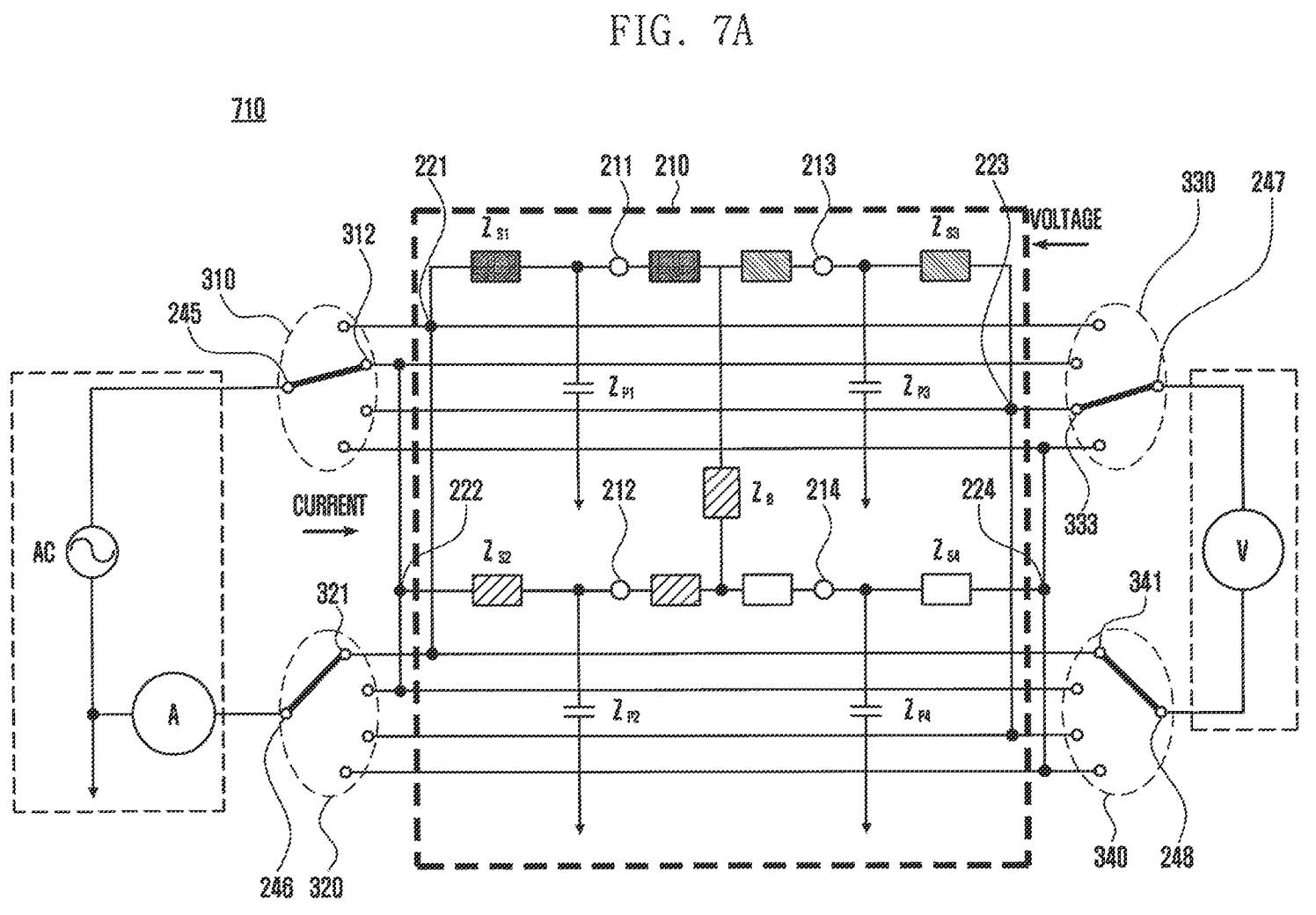
Figure 7B:
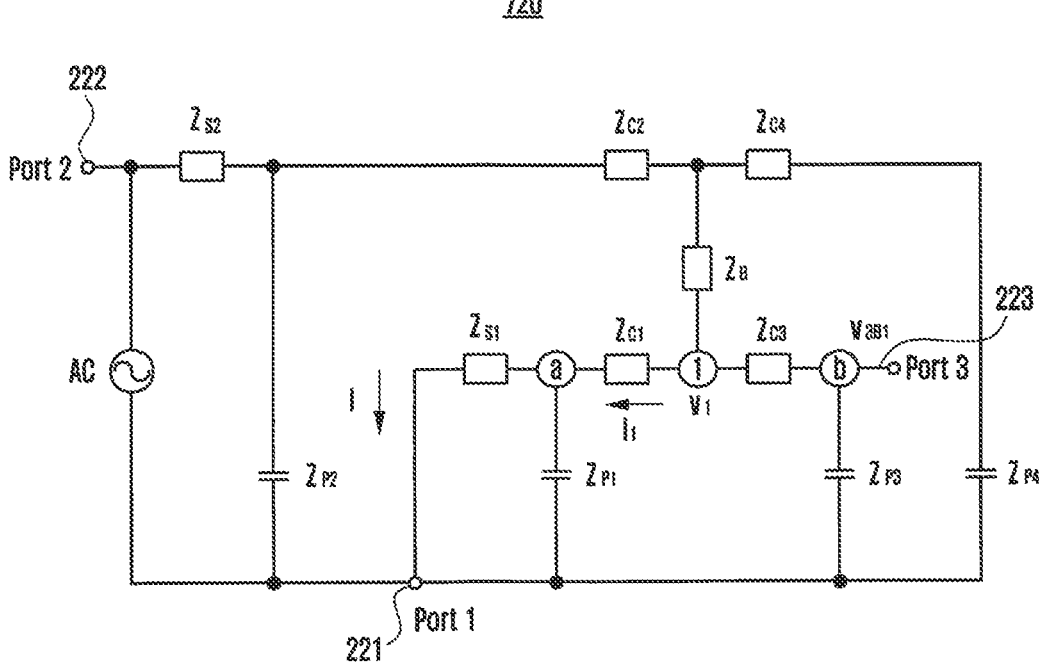
FIG. 7B illustrates an equivalent circuit corresponding to the current-voltage path of FIG. 7A.

FIG. 7A illustrates a current-voltage path 710 configured in the bio-contact circuit 210 according to the third control signal of Table 1, and FIG. 7B is an equivalent circuit 720 corresponding to the current-voltage path 710 of FIG. 7A.

Referring to FIG. 7A, in response to the third control signal, the first switch 310 may connect the feed port 245 to the 1-2 terminal 312, the second switch 320 may connect the current measurement port 246 to the 2-1 terminal 321, the third switch 330 may connect the first voltage measurement port 247 to the 3-3 terminal 333, and the fourth switch 340 may connect the second voltage measurement port 248 to the 4-1 terminal 341. Accordingly, current i may flow from the second port 222 to the first port 221, and the voltage V3B1 may be measured in a direction going from the third port 223 to the first port 221.

Referring to FIG. 7B, a current may leak through the parasitic impedance ZP1 at node a, and a compensation value k10 for compensating for the current i may be expressed by Equation 6.

$$k_{10} \overset{\Delta}{=} \frac{Z_{P1} + Z_{S1}}{Z_{P1}} \qquad \text{[Equation 6]}$$

Even at node b, a voltage may leak (e.g., a voltage drop) due to the influence of the parasitic component $Z_{P3}$, and a compensated voltage value v1 at node 1 may be expressed as the right side of Equation 7. The voltage value v1 calculated using the impedances $Z_{C1}$, $Z_{S1}$, and $Z_{P1}$ between node 1 and the first port 221 and the compensation value $K_{10}$ may be expressed as the left side of Equation 7.

$$k_{10}i(Z_{C1} + Z_{S1}\|Z_{P1}) = \frac{Z_{C3} + Z_{P3}}{Z_{P3}}v_{3B1} \qquad \text{[Equation 7]}$$

Equation 7 includes the contact impedance ZC1 of the first electrode 211 to be obtained and the contact impedance ZC3 of the third electrode 213 to be obtained. That is, since ZC1 and ZC3 may not be obtained using Equation 7 alone, another Equation expressed by ZC1 and ZC3 is required. This equation can be obtained by changing the current-voltage path of the bio-contact circuit 210.

Figure 8A:
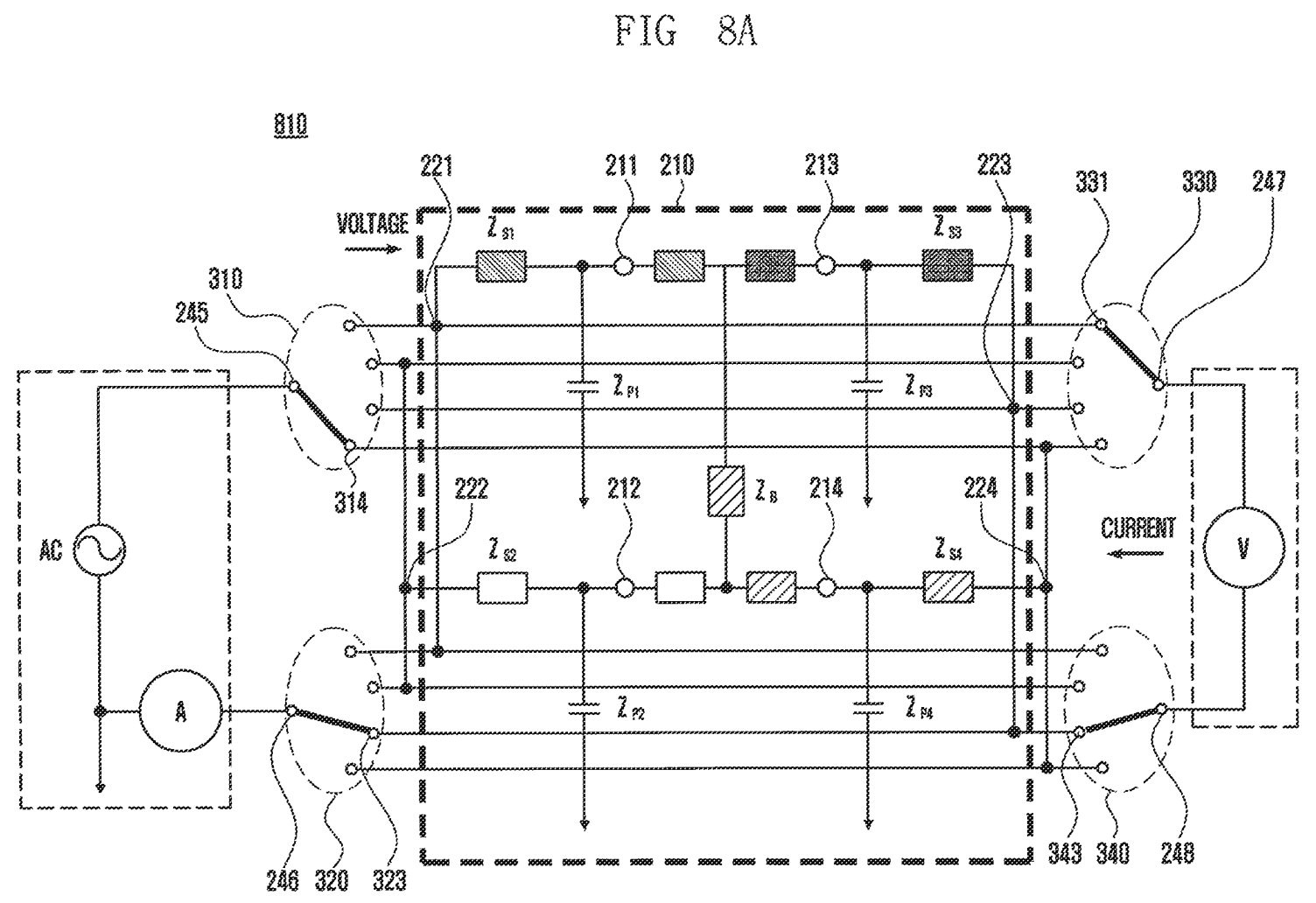
Figure 8B:
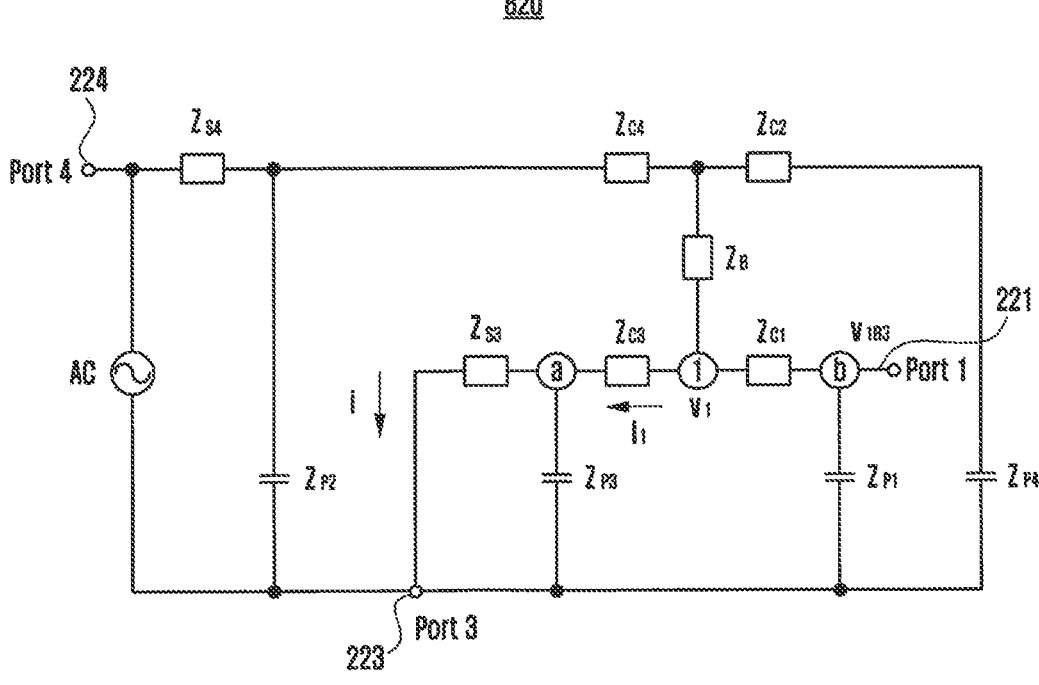
FIG. 8B illustrates an equivalent circuit corresponding to the current-voltage path of FIG. 8A.

FIG. 8A illustrates a current-voltage path 810 configured in the bio-contact circuit 210 according to the fourth control signal of Table 1, and FIG. 8B is an equivalent circuit 810 corresponding to the current-voltage path 810 of FIG. 8A.

Referring to FIG. 8A, in response to the fourth control signal, the first switch 310 may connect the feed port 245 to the 1-4 terminal 314, the second switch 320 may connect the current measurement port 246 to the 2-3 terminal 323, the third switch 330 may connect the first voltage measurement port 247 to the 3-1 terminal 331, and the fourth switch 340 may connect the second voltage measurement port 248 to the 4-3 terminal 343. Accordingly, current i may flow from the fourth port 224 to the third port 223, and the voltage V1B3 may be measured in a direction going from the first port 221 to the third port 223.

$$k_{12} \overset{\Delta}{=} \frac{Z_{P3} + Z_{S3}}{Z_{P3}} \qquad \text{[Equation 8]}$$

Even at node b, a voltage may leak (e.g., a voltage drop) due to the influence of the parasitic component $Z_{P1}$, and a compensated voltage value v1 at node 1 may be expressed as the right side of Equation 9. The voltage value v1 calculated using the impedances $Z_{C3}$, $Z_{S3}$, and $Z_{P3}$ between node 1 and the third port 223 and the compensation value $K_{12}$ may be expressed as the left side of Equation 9.

$$k_{12}i(Z_{C3} + Z_{S3} \| Z_{P3}) = \frac{Z_{C1} + Z_{P1}}{Z_{P1}} v_{1B3} \qquad \text{[Equation 9]}$$

The processor (e.g., the processor 260 of FIG. 2 or the impedance calculation module 423 of FIG. 4) may obtain the third impedance measurement value $Z_{3B1}$ from the current value and voltage value $V_{3B1}$ measured through the current-voltage path 710 of FIG. 7A. The processor 260 may obtain a fourth impedance measurement value $Z_{1B3}$ from the current value and voltage value $V_{1B3}$ measured through the current-voltage path 810 of FIG. 8A.

The processor (e.g., the processor 260 of FIG. 2 or the second leakage compensation module 440 of FIG. 4) may obtain the contact impedance $Z_{C1}$ of the first electrode 211 and the contact impedance $Z_{C3}$ of the third electrode 213, by using Equation 10 expressed by combining Equation 7 with Equation 9.

$$\begin{bmatrix} Z_{C1} \\ Z_{C3} \end{bmatrix} = \begin{bmatrix} k_{10}Z_{P3} & -Z_{3B1} \\ -Z_{1B3} & k_{12}Z_{P1} \end{bmatrix}^{-1} \begin{bmatrix} Z_{P3}(Z_{3B1} - Z_{S1}) \\ Z_{P1}(Z_{1B3} - Z_{S3}) \end{bmatrix} \qquad \text{[Equation 10]}$$

Figure 9A:
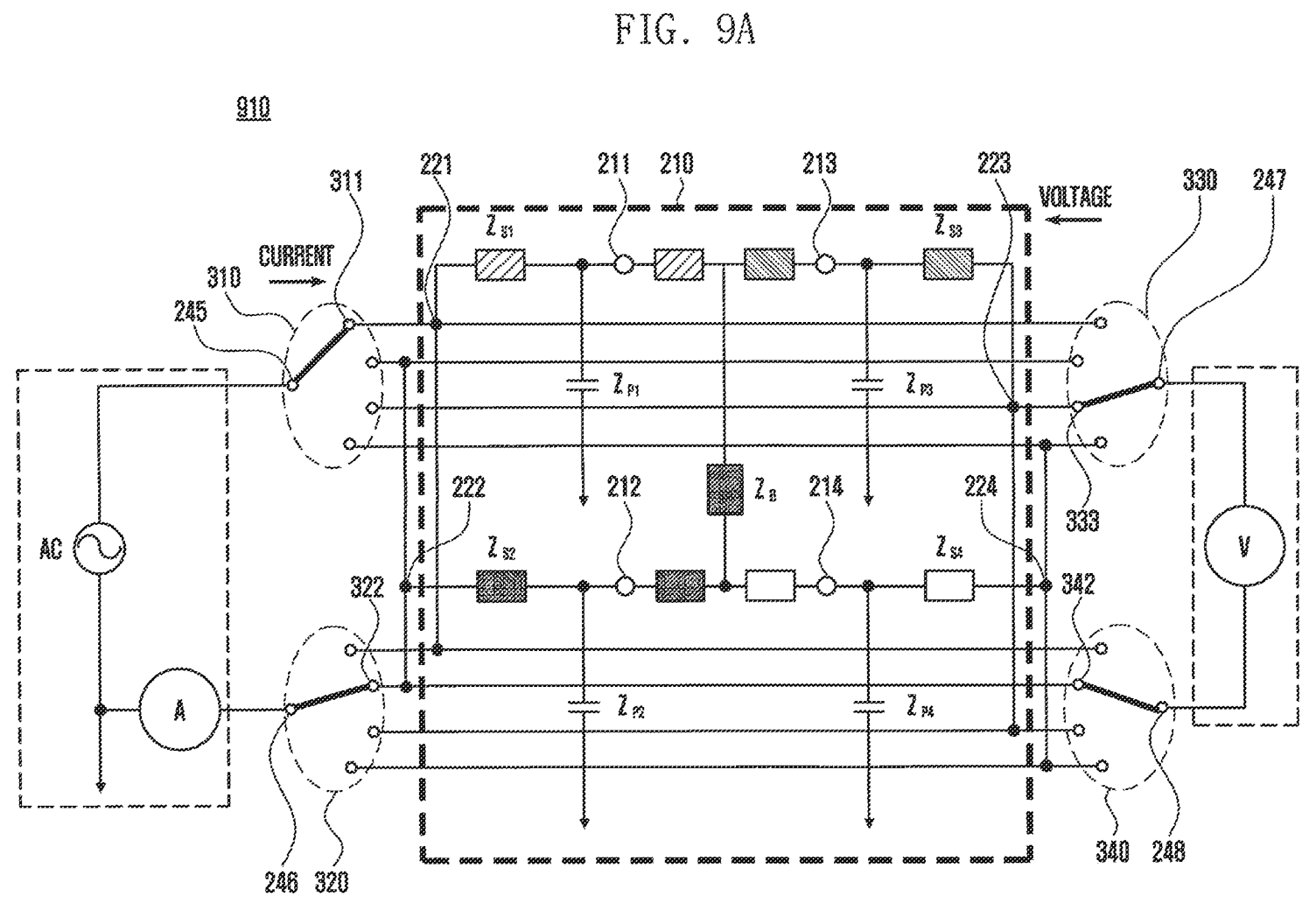
Figure 9B:
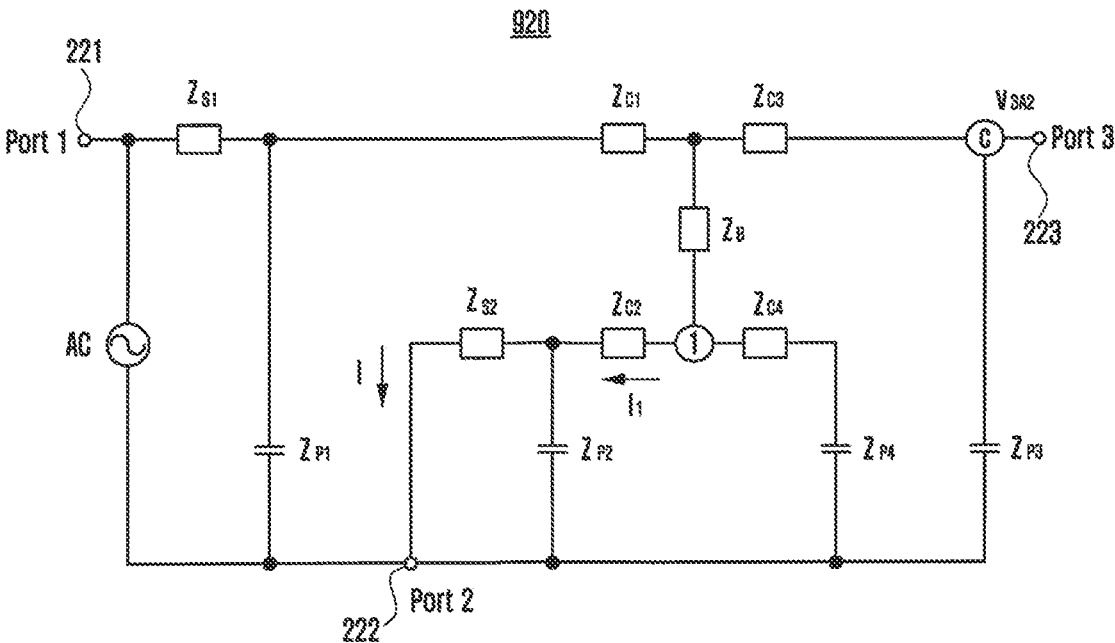
FIG. 9B illustrates an equivalent circuit corresponding to the current-voltage path of FIG. 9A.

FIG. 9A illustrates a current-voltage path 910 configured in the bio-contact circuit 210 according to the fifth control signal of Table 1, and FIG. 9B is an equivalent circuit 920 corresponding to the current-voltage path 910 of FIG. 9A.

Referring to FIG. 9A, in response to the fifth control signal, the first switch 310 may connect the feed port 245 to the 1-1 terminal 311, the second switch 320 may connect the current measurement port 246 to the 2-2 terminal 322, the third switch 330 may connect the first voltage measurement port 247 to the 3-3 terminal 333, and the fourth switch 340 may connect the second voltage measurement port 248 to the 4-2 terminal 342. Accordingly, current i may flow from the first port 221 to the second port 222, and the voltage V3B2 may be measured in a direction going from the third port 223 to the second port 222.

Referring to FIG. 9B, a current may leak through the parasitic impedances ZP2 and ZP4 at node 1, and a compensation value k21 for compensating for the current i may be expressed by Equation 11.

$$k_{21} \triangleq k_{11} \frac{Z_{C2} + Z_{S2} \| Z_{P2} + Z_{C4} + Z_{P4}}{Z_{C4} + Z_{P4}} \qquad \text{[Equation 11]}$$

In FIG. 9B, a value obtained by combining the impedances at node 1 may be expressed by Equation 12.

$$\ell_1 \triangleq (Z_{C2} + Z_{S2} \| Z_{P2}) \| (Z_{C4} + Z_{P4}) \qquad \text{[Equation 12]}$$

Even at node c, a voltage may leak (e.g., a voltage drop) due to the influence of the parasitic component $Z_{P3}$, and a compensated voltage value may be expressed by Equation 13.

$$k_{21}i(Z_B + \ell_1) = \frac{Z_{C3} + Z_{P3}}{Z_{P3}} v_{3A2} \qquad \text{[Equation 13]}$$

The processor (e.g., the processor 260 of FIG. 2 or the impedance calculation module 423 of FIG. 4) may obtain the fifth impedance measurement value $Z_3$ from the current value and voltage value $V_{3A2}$ measured through the current-voltage path 910 of FIG. 9A.

The processor (e.g., the processor 260 of FIG. 2 or the third leakage compensation module 450 of FIG. 4) may obtain the bio-impedance ZB using Equation 13 or Equation 14 converted therefrom.

$$z_B = \frac{Z_{BA2}(Z_{C3} + Z_{P3})}{k_{21}Z_{P3}} - \ell_1 \qquad \text{[Equation 14]}$$

As a result of the simulation, according to a method of measuring bio-impedance by connecting the first to fourth ports 221, 222, 223, and 224 to the feeding port or to the second voltage measurement ports 245, 246, 247, and 248 in a one-to-one correspondence relationship, it has been identified that an error ranging from −31.8% to 83.0% has occurred due to the influence of the leakage of an electrical signal. In a measurement method using a switch according to Reference 6 (KR Publication No. 10-2017-0041511), it has been identified that an error ranging from −46.9% to 46.5% has occurred. In a measurement method using Equations 10 to 14 of Reference 6, it has been identified that an error ranging from −46.6% to 47.9% has occurred. On the other hand, in a measurement method using the control operation shown in Table 1, it has been identified that the error has been greatly improved by about −0.8% to 0.9%.

Figure 10A:
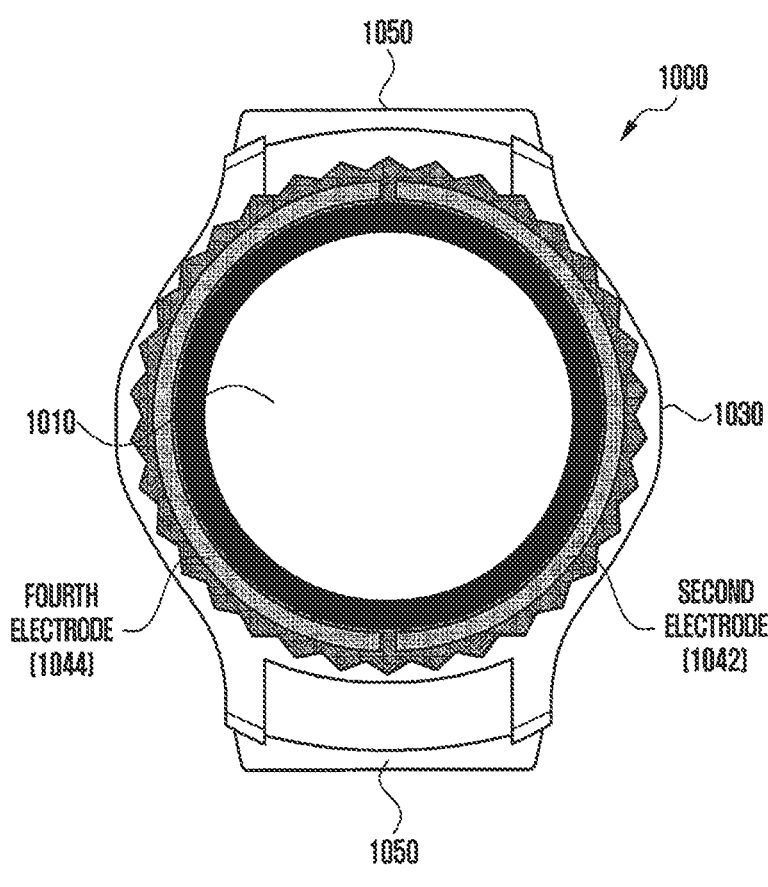
FIG. 10A illustrates a front surface of an electronic device according to an embodiment.
Figure 10B:
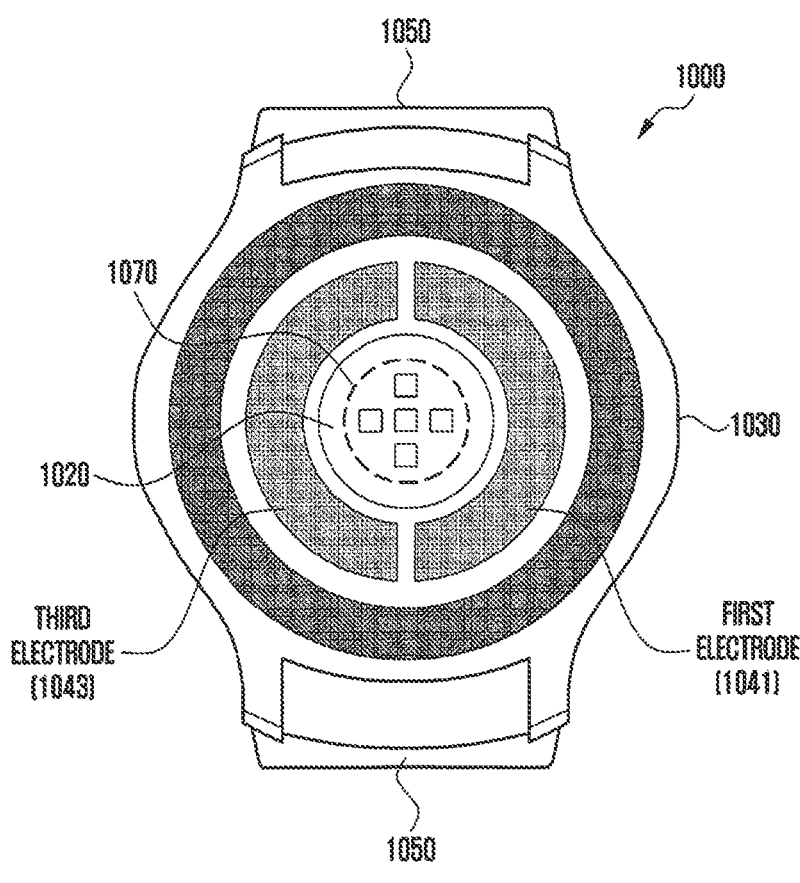
FIG. 10B illustrates a rear surface of the electronic device.
Figure 10C:
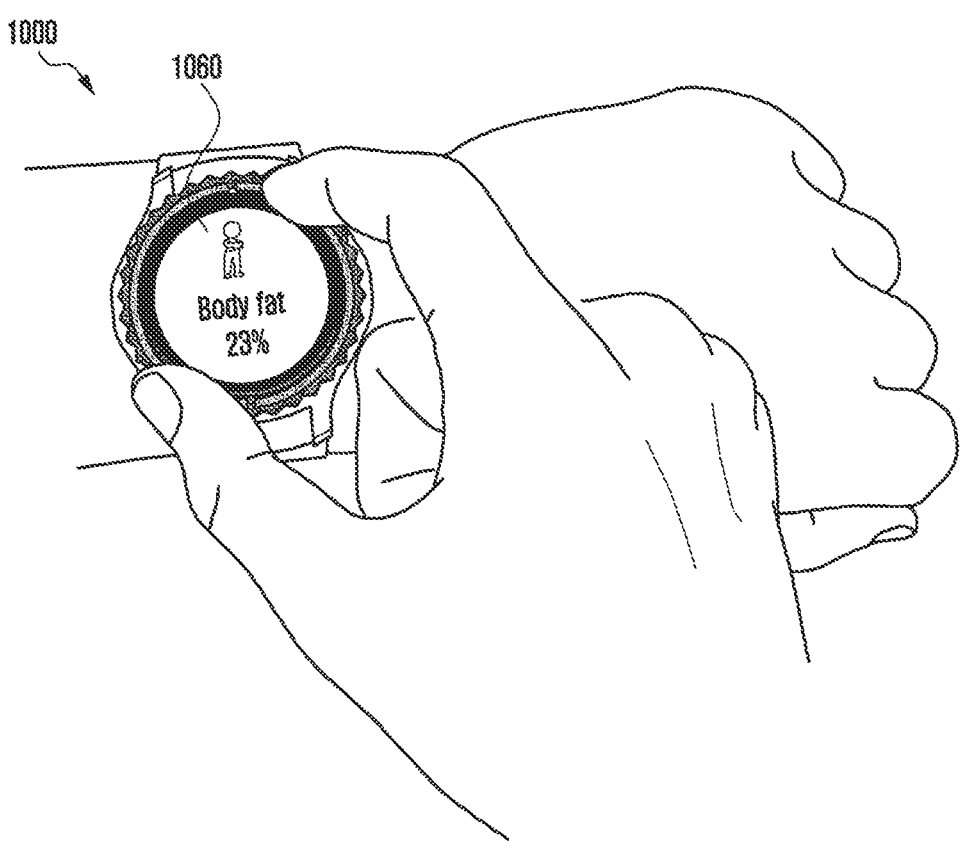
FIG. 10C illustrates an example of biometric measurement using the electronic device.

FIG. 10A illustrates a front surface of an electronic device 1000 according to an embodiment, FIG. 10B illustrates a rear surface of the electronic device 1000, and FIG. 10C illustrates an example of biometric measurement using the electronic device 1000.

Referring to FIGS. 10A and 10B, the electronic device 1000 (e.g., the electronic device 200 of FIG. 2) may include: a housing including a first surface (or front surface) 1010, a second surface (or rear surface) 1020, and a side surface 1030 surrounding a space between the first surface 1010 and the second surface 1020, and binding members 1050 connected to at least a portion of the housing and configured to detachably bind the electronic device 1000 on a portion of a user's body (e.g., wrist). In another embodiment (not shown), the housing may refer to a structure forming a part of the first surface 1010, the second surface 1020, and the side surface 1030.

According to an embodiment, the first surface 1010 may be formed of a front plate (e.g., a glass plate including various coating layers, or a polymer plate), at least a portion of which is substantially transparent. A display may be visually seen through a substantial portion of the first surface 1010. The first surface 1010 may include a second electrode 1042 (e.g., the second electrode 212 in FIG. 2) and a fourth electrode 1044 (e.g., the fourth electrode 214 in FIG. 2). The second electrode 1042 and the fourth electrode 1044 may be electrically connected to a current-voltage measurement module (for example, the current-voltage measurement module 240 in FIG. 2) located in the housing through a current-voltage path configuration module (e.g., the current-voltage path configuration module 250 of FIG. 2).

According to an embodiment, the second surface 1020 may be formed of a substantially opaque rear plate. The second surface 1020 may include a first electrode 1041 (e.g., the first electrode 211 in FIG. 2), a third electrode 1043 (e.g., the third electrode 213 in FIG. 2), and a photoplethysmogram (PPG) sensor 1070. The first electrode 1041 and the third electrode 1043 may be electrically connected to the current-voltage measurement module through the current-voltage path configuration module.

Referring to FIG. 10C, a user wears the electronic device 1000 on a wrist such that the first electrode 1041 and the third electrode 1043 come in contact with the wrist, and makes contact with the second electrode 1042 and the fourth electrode 1044 by using a finger. The processor of the electronic device 1000 (for example, the processor 260 of FIG. 2) may obtain a bio-impedance value, measure the user's state by using the bio-impedance value, and display a measurement result 1060 on the display.

Figure 11A:
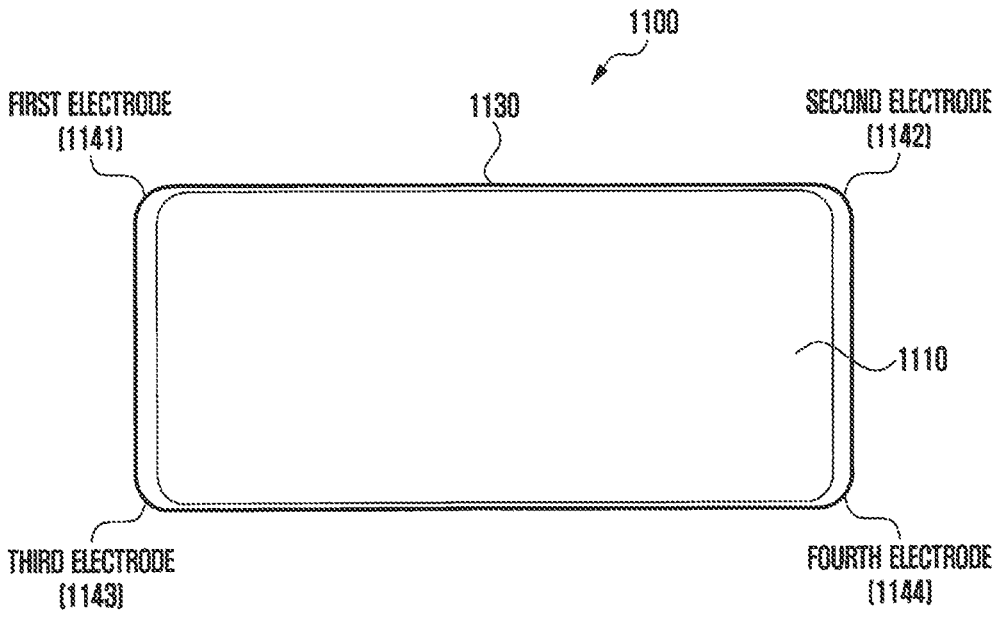
FIG. 11A illustrates a front view of an electronic device according to an embodiment.
Figure 11B:
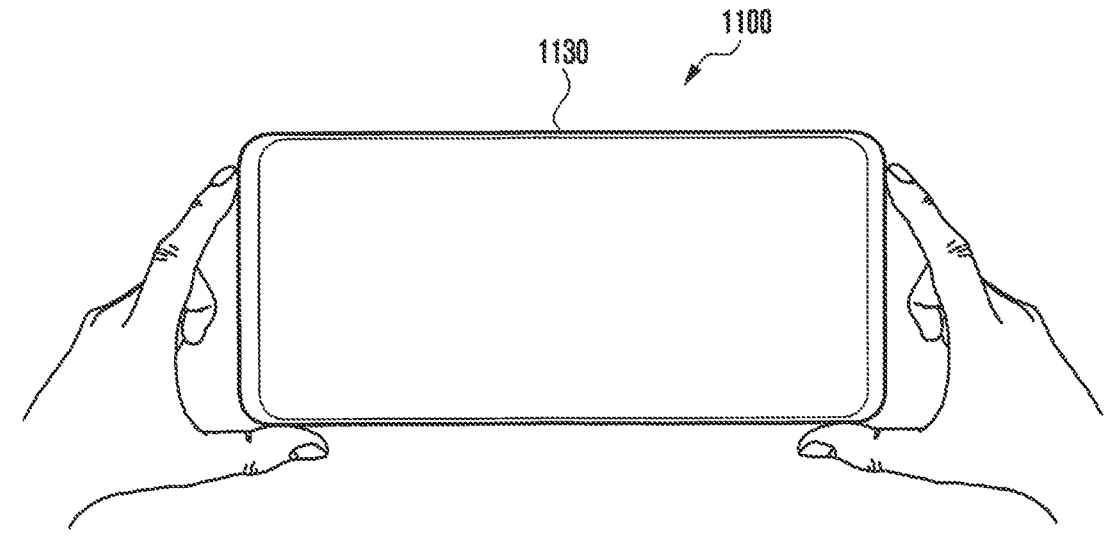
FIG. 11B illustrates an example of biometric measurement using the electronic device.

FIG. 11A illustrates a front surface of an electronic device 1100 according to an embodiment, and FIG. 11B illustrates an example of a biometric measurement using the electronic device 1100.

Referring to FIG. 11A, the electronic device 1100 (e.g., the electronic device 200 of FIG. 2) may include a housing including a first surface (or a front surface) 1110, a second surface (or a rear surface) (not shown), and a side surface 1030 surrounding a space between the first surface 1110 and the second surface. A display may be visually seen through a substantial portion of the first surface 1110. In another embodiment (not shown), the housing may refer to a structure forming a part of the first surface 1110, the second surface, and the side surface 1130.

According to an embodiment, the side surface 1130 is coupled to a front plate forming at least a portion of the first surface 1110 and a rear plate forming at least a portion of the second surface, and may be formed of a side bezel structure (or a side member) including a metal and/or a polymer. In some embodiments, the rear plate and the side bezel structure may be integrally formed, and may include the same material (e.g., a metal material such as aluminum). The electrodes 1141, 1142, 1143, and 1144 may be disposed at four corners of the side surface 1130, respectively. For example, when viewed from above the first surface 1110 in a state in which the housing of the electronic device 1100 has a rectangular shape and one of the short sides is oriented toward the left and the other thereof is oriented toward the right, the first electrode 1141 and the third electrode 1143 may be disposed on the left side, and the second electrode 1142 and the fourth electrode 1144 may be disposed on the right side. Accordingly, the user may hold the first electrode 1141 and the third electrode 1143 with one hand, and hold the second electrode 1142 and the fourth electrode 1144 with the other hand. The electrodes 1141, 1142, 1143, and 1144 may be electrically connected to a current-voltage measurement module (e.g., the current-voltage measurement module 240 of FIG. 2) located in the housing through a current-voltage path configuration module (e.g., the current-voltage path configuration module 250 of FIG. 2).

Referring to FIG. 11B, the user holds the four corners of the electronic device 1100 with both hands such that the first electrode 1141 and the third electrode 1143 come in contact with the left hand and the second electrode 1142 and the fourth electrode 1144 come in contact with the right hand. The processor of the electronic device 1100 (e.g., the processor 260 of FIG. 2) may obtain a value of the bio-impedance, measure a user's state by using the acquired bio-impedance value, and display a measurement result on a display.

Figure 12A:
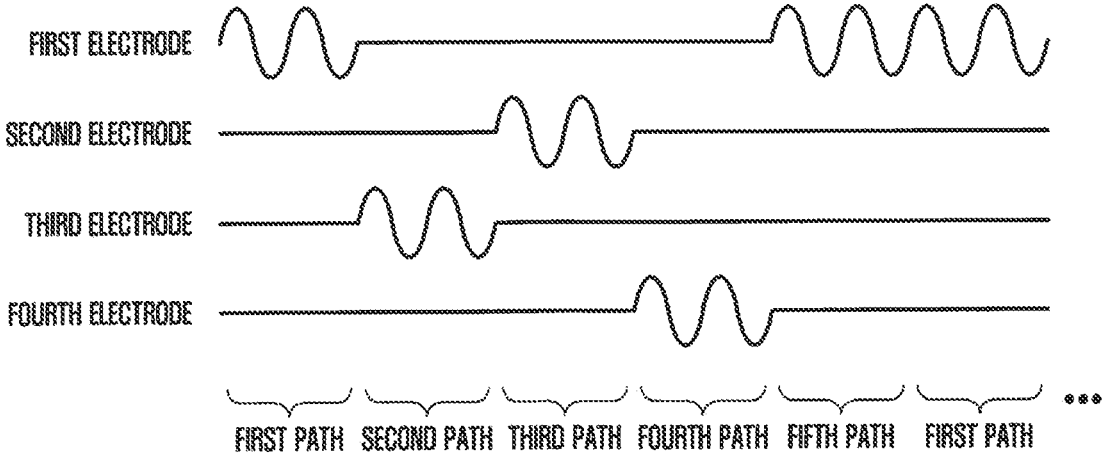
FIG. 12A illustrates an oscilloscope waveform that appears when the body does not come in contact with four electrodes.
Figure 12B:
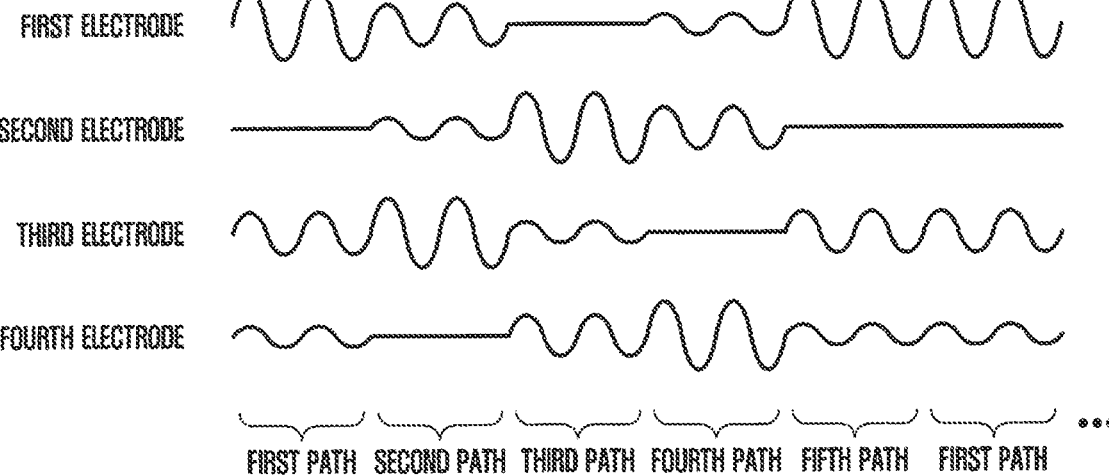
FIG. 12B illustrates an oscilloscope waveform that appears when the body comes in contact with four electrodes.

FIG. 12A illustrates an oscilloscope waveform that appears when the body does not come in contact with four electrodes, and FIG. 12B illustrates an oscilloscope waveform that appears when the body comes contact with four electrodes. Referring to FIG. 12A and Table 1, it may be identified that an electrical signal is measured only in an electrode to which a current is applied. Referring to FIG. 12B and Table 1, it may be identified that the largest signal is measured at the electrode to which the current is applied, and different sized electrical signals are measured at the remaining electrodes according to control conditions, i.e., polarity swapping ON/OFF and current-voltage swapping ON/OFF.

Figure 13:
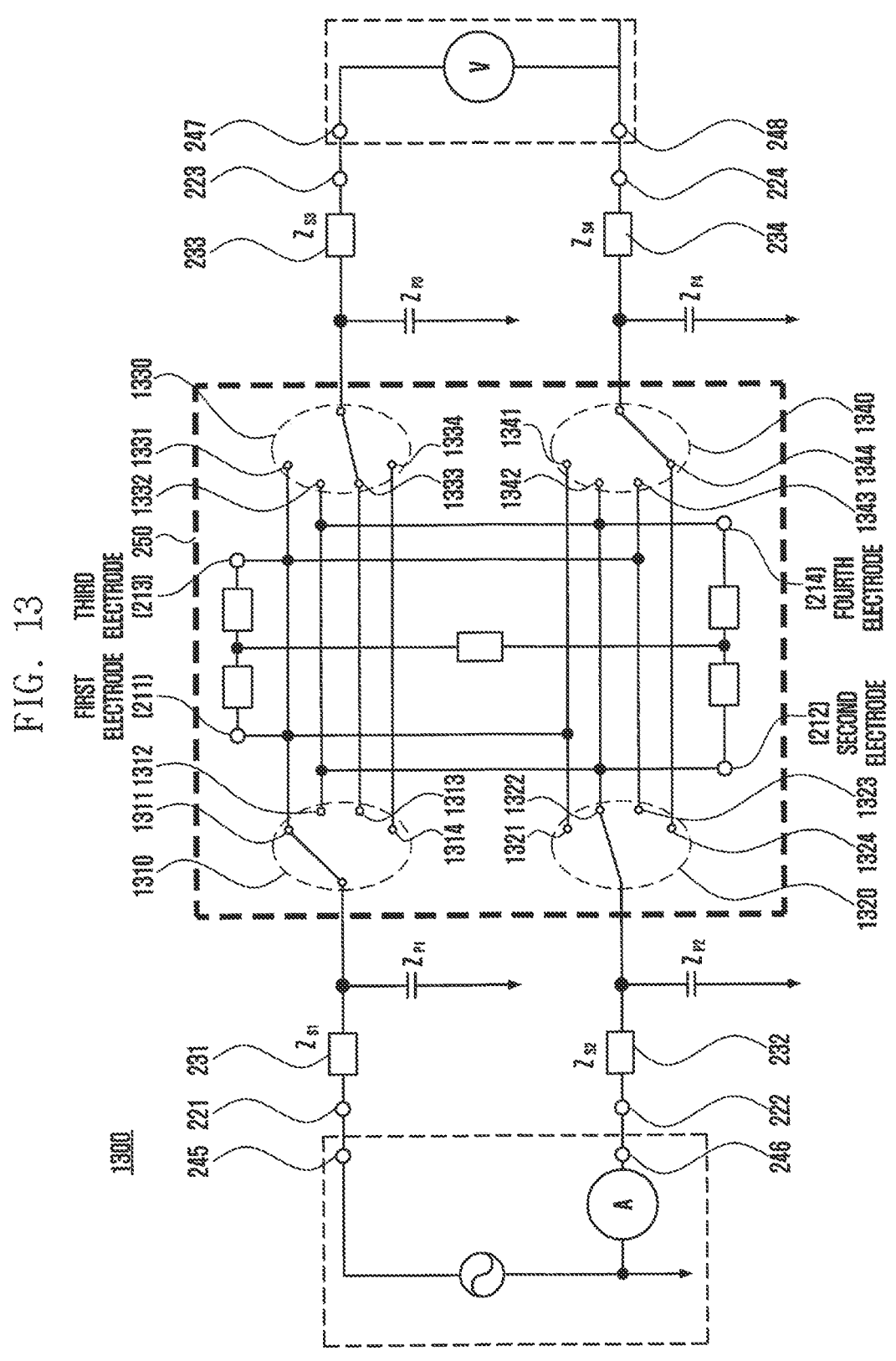
FIG. 13 is a circuit diagram of a path configuration module according to various embodiments of the disclosure.

FIG. 13 is a circuit diagram 1300 of a path configuration module 250 according to various embodiments of the disclosure. Referring to FIG. 13, the first to fourth ports 221, 222, 223, and 224 may be connected to the feeding port or to the second voltage measurement ports 245, 246, 247 and 248, respectively. The path configuration module 250 may include four switches 1310, 1320, 1330, and 1340 each having four terminals.

A 1-1 terminal 1311, a 1-2 terminal 1312, a 1-3 terminal 1313, and a 1-4 terminal 1314 of the first switch 1310 may be electrically connected to the first electrode 211, the second electrode 212, the third electrode 213, and the fourth electrode 214, respectively, and the first switch 1310 may connect the feeding port 32) 245 to one of the electrodes 211, 212, 213, and 214 under the control of the processor 260.

A 2-1 terminal 1321, a 2-2 terminal 1322, a 2-3 terminal 1323, and a 2-4 terminal 1324 of the second switch 1320 may be electrically connected to the first electrode 211, the second electrode 212, the third electrode 213, and the fourth electrode 214, respectively, and the second switch 1320 may connect the current measurement port 246 to one of the electrodes 211, 212, 213, and 214 under the control of the processor 260.

A 3-1 terminal 1331, a 3-2 terminal 1332, a 3-3 terminal 1333, and a 3-4 terminal 1334 of the third switch 1330 may be electrically connected to the first electrode 211, the second electrode 212, the third electrode 213, and the fourth electrode 214, respectively, and the third switch 1330 may connect the first voltage measurement port 247 to one of the electrodes 211, 212, 213, and 214 under the control of the processor 260.

A 4-1 terminal 1341, a 4-2 terminal 1342, a 4-3 terminal 1343, and a 4-4 terminal 1344 of the fourth switch 1340 may be electrically connected to the first electrode 211, the second electrode 212, the third electrode 213, and the fourth electrode 214, respectively, and the fourth switch 1340 may connect the second voltage measurement port 248 to one of the electrodes 211, 212, 2133, and 214 under the control of the processor 260.

According to various embodiments, the processor 260 may control the switches 1310, 1320, 1330, and 1340 in the same operation as the operation in Table 1, and thus may acquire contact impedances ZC1, ZC2, ZC3, and ZC4 and the bio-impedance ZB.

According to various embodiments of the disclosure, an electronic device may include: a bio-contact circuit having four electrodes (e.g., the bio-contact circuit 210 of FIG. 2); a current-voltage measurement module (e.g., the current-voltage measurement module 240 of FIG. 2) including a feeding port, a current measurement port, a first voltage measurement port, a second voltage measurement port, an alternating-current signal generator electrically connected to the feeding port, an ammeter electrically connected to the current measurement port, and a voltmeter electrically connected between the first voltage measurement port and the second voltage measurement port; a processor (e.g., the processor 260 of FIG. 2); a memory (e.g., the memory 130 of FIG. 1) electrically connected to the processor, and configured to store a characteristic impedance value of a circuit element electrically connected between the current-voltage measurement module and the bio-contact circuit and to store a value of parasitic impedance caused by a parasitic component existing between the bio-contact circuit and a ground; and a current-voltage path configuration module (e.g., the current-voltage path configuration module 250 of FIG. 2) configured to electrically connect the bio-contact circuit to the feeding port, the current measurement port, the first voltage measurement port, and the second voltage measurement port such that a voltage path and a current path of the bio-contact circuit are changed under the control of the processor, wherein the memory stores instructions which, when executed, cause the processor to: control the current-voltage path configuration module to sequentially configure a first current-voltage path, a second current-voltage path, a third current-voltage path, and a fourth current-voltage path in the bio-contact circuit such that, in connection with each of the current-voltage paths, one of two electrodes of the voltage path matches with one of two electrodes of the current path, and no bio-impedance is included on the voltage path; receive, from the current-voltage measurement module, first current/voltage values measured in a state in which the first current-voltage path constitutes the bio-contact circuit, and obtain a first impedance measurement value by using the first current/voltage values; receive, from the current-voltage measurement module, second current/voltage values measured in a state in which the second current-voltage path constitutes the bio-contact circuit, and obtain a second impedance measurement value by using the second current/voltage values; receive, from the current-voltage measurement module, third current/voltage values measured in a state in which the third current-voltage path constitutes the bio-contact circuit, and obtain a third impedance measurement value by using the third current/voltage values; receive, from the current-voltage measurement module, fourth current/voltage values measured in a state in which the fourth current-voltage path constitutes the bio-contact circuit, and obtain a fourth impedance measurement value by using the fourth current/voltage values; correct the first impedance measurement value, the second impedance measurement value, the third impedance measurement value, and the fourth impedance measurement value by using the characteristic impedance value and the parasitic impedance value, so as to obtain contact impedance values of the four electrodes, respectively; control the current-voltage path configuration module to configure a fifth current-voltage path in the bio-contact circuit such that one of two electrodes of the fifth voltage path matches with one of two electrodes of the fifth current path and the bio-impedance is included on the fifth current path and the fifth voltage path; receive, from the current-voltage measurement module, fifth current/voltage values measured in a state in which the fifth current-voltage path constitutes the bio-contact circuit, and obtain a fifth impedance measurement value by using the fifth current/voltage values; and acquire the bio-impedance value by using contact impedance values of electrodes located on at least the fifth voltage path among the contact impedance values, the fifth impedance measurement value, the characteristic impedance value, and the parasitic impedance value.

In various embodiments, the electronic device may further include a housing including a first surface, a second surface, and a side surface surrounding a space between the first surface and the second surface, wherein two electrodes among the four electrodes are disposed on the first surface (e.g., the first surface 1010 of FIG. 10A), and the other two electrodes are disposed on the second surface (e.g., the second surface 1020 of FIG. 10B). The display may be visually seen through one of the first surface and the second surface.

In various embodiments, a first electrode and a third electrode may be disposed on one of the first surface and the second surface, and a second electrode and a fourth electrode may be disposed on the other one of the first surface and the second surface. The first current-voltage path (e.g., the current-voltage path 510 of FIG. 5A) may include a first current path established from the first electrode to the second electrode and a first voltage path established from the fourth electrode to the second electrode. The second current-voltage path (e.g., the current-voltage path 610 of FIG. 6A) may include a second current path established from the third electrode to the fourth electrode and a second voltage path established from the second electrode to the fourth electrode. The third current-voltage path (e.g., the current-voltage path 710 of FIG. 7A) may include a third current path established from the second electrode to the first electrode and a third voltage path established from the third electrode to the first electrode. The fourth current-voltage path (e.g., the current-voltage path 810 of FIG. 8A) may include a fourth current path established from the fourth electrode to the third electrode and a fourth voltage path established from the first electrode to the third electrode.

In various embodiments, the instructions may cause the processor to: acquire a contact impedance value of the second electrode and a contact impedance value of the fourth electrode, by using (e.g., using equation 5) the first impedance measurement value, the second impedance measurement value, a value of parasitic impedance caused by a parasitic component existing between the second electrode and a ground, a value of parasitic impedance caused by a parasitic component existing between the fourth electrode and the ground, a characteristic impedance value of a circuit element connected to the second electrode, and a characteristic impedance value of a circuit element connected to the fourth electrode; and acquire a contact impedance value of the first electrode and a contact impedance value of the third electrode, by using (e.g., using equation 10) the third impedance measurement value, the fourth impedance measurement value, a value of parasitic impedance caused by a parasitic component existing between the first electrode and a ground, a value of parasitic impedance caused by a parasitic component existing between the third electrode and the ground, a characteristic impedance value of a circuit element connected to the first electrode, and a characteristic impedance value of a circuit element connected to the third electrode.

In various embodiments, the instructions may cause the processor to acquire a value of the bio-impedance by using (e.g., using equations 11 to 14) contact impedance values of electrodes located on the fifth voltage path, contact impedance values of electrodes that are not located on the fifth current-voltage path, a characteristic impedance value of a circuit element connected to an electrode commonly existing on the fifth voltage path and the fifth current path, a value of parasitic impedance caused by a parasitic component existing between electrodes located on the fifth voltage path and a ground, and a value of parasitic impedance caused by a parasitic component existing between an electrode that is not located on the fifth current-voltage path and the ground.

In various embodiments, the fifth current path and the fifth voltage path each may include: a current-voltage path including the first current path and a voltage path established from the third electrode to the second electrode (e.g., a voltage path of No. 5 in Table 1); a current-voltage path including the second current path and a voltage path established from the first electrode to the fourth electrode (e.g., a voltage path of No. 6 in Table 1); a current-voltage path including the third current path and a voltage path established from the fourth electrode to the first electrode (e.g., a voltage path of No. 7 in Table 1); or a current-voltage path including the fourth current path and a voltage path established from the second electrode to the third electrode (e.g., a voltage path of No. 8 in Table 1).

In various embodiments, the electronic device may further include a rectangular-shaped housing including a first surface, a second surface, and a side surface (e.g., the side surface 1130 of FIG. 11A) surrounding a space between the first surface and the second surface, and the four electrodes are disposed on the four corners of the side surface, respectively. When viewed from above the first surface in a state in which one of the shorter sides of the housing is oriented toward the left and the other one is oriented toward the right, two of the four electrodes may be disposed on the left side, and the other two electrodes may be disposed on the right side of the electronic device.

In various embodiments, the current-voltage path configuration module may include: a first switch connecting the feeding port to one of the four electrodes under the control of the processor; a second switch connecting the current measuring port to one of the four electrodes under the control of the processor; a third switch connecting the first voltage measurement port to one of the four electrodes under the control of the processor; and a fourth switch connecting the second voltage measurement port to one of the four electrodes under the control of the processor.

In various embodiments, the circuit element may include an electronic component that removes a DC component from an electrical signal flowing from the current-voltage measurement module to the bio-contact circuit.

In various embodiments, the circuit element may include a first circuit element connected to the first electrode, a second circuit element connected to the second electrode, a third circuit element connected to the third electrode, and a fourth circuit element connected to the fourth electrode, wherein the first circuit element is connected to one of the feeding port, current measurement port, first voltage measurement port, and second voltage measurement port by means of the first switch (e.g., the first switch 310 of FIG. 3). The second circuit element may be connected to one of the feeding port, current measurement port, first voltage measurement port, and second voltage measurement port by means of the second switch (e.g., the second switch 320 of FIG. 3). The third circuit element may be connected to one of the feeding port, current measurement port, first voltage measurement port, and second voltage measurement port by means of the third switch (e.g., the third switch 330 of FIG. 3). The fourth circuit element may be connected to one of the feeding port, current measurement port, first voltage measurement port, and second voltage measurement port by means of the fourth switch (e.g., the fourth switch 340 of FIG. 3).

In various embodiments, the circuit element may include a first circuit element connected to the feeding port, a second circuit element connected to the current measurement port, a third circuit element connected to the first voltage measurement port, and a fourth circuit element connected to the second voltage measurement port, wherein the first circuit element is connected to one of the four electrodes by means of the first switch (e.g., the first switch 1310 of FIG. 13). The second circuit element may be connected to one of the four electrodes by means of a second switch (e.g., the second switch 1320 of FIG. 13). The third circuit element may be connected to one of the four electrodes by means of the third switch (e.g., the third switch 1330 of FIG. 13). The fourth circuit element may be connected to one of the four electrodes by means of the fourth switch (e.g., the fourth switch 1340 of FIG. 13).

The embodiments of the disclosure provided in the specification and drawings are suggested for easy explanation and understanding of the technical features according to the embodiments of the disclosure, and are not intended to limit the scope of the embodiments of the disclosure. Therefore, the scope of various embodiments of the disclosure should be interpreted as including all changes or modified forms derived based on the technical idea of various embodiments of the disclosure.

The invention claimed is:

1. An electronic device comprising:
a bio-contact circuit comprising four electrodes;
a current-voltage measurement module comprising a feeding port, a current measurement port, a first voltage measurement port, a second voltage measurement port, an alternating-current signal generator electrically connected to the feeding port, an ammeter electrically connected to the current measurement port, and a voltmeter electrically connected between the first voltage measurement port and the second voltage measurement port;
a processor;
a memory electrically connected to the processor and configured to store a characteristic impedance value of a plurality of circuit elements electrically connected between the current-voltage measurement module and the bio-contact circuit and to store a value of parasitic impedance caused by a parasitic component existing between the bio-contact circuit and a ground; and
a current-voltage path configuration module configured to electrically connect the bio-contact circuit to the feeding port, the current measurement port, the first voltage measurement port, and the second voltage measurement port such that a voltage path and a current path on the bio-contact circuit are changed under the control of the processor,
wherein the memory stores instructions which, when executed, cause the processor to:
control the current-voltage path configuration module to sequentially configure a first current-voltage path, a second current-voltage path, a third current-voltage path, and a fourth current-voltage path in the bio-contact circuit such that:
one of two electrodes of the first voltage path matches with one of two electrodes of the first current path, and no bio-impedance is included on the first voltage path,
one of two electrodes of the second voltage path matches with one of two electrodes of the second current path, and no bio-impedance is included on the second voltage path,
one of two electrodes of the third voltage path matches with one of two electrodes of the third current path, and no bio-impedance is included on the third voltage path, and
one of two electrodes of the fourth voltage path matches with one of two electrodes of the fourth current path, and no bio-impedance is included on the fourth voltage path;
receive, from the current-voltage measurement module, first current/voltage values measured in a state in which the first current-voltage path constitutes the bio-contact circuit, and obtain a first impedance measurement value by using the first current/voltage values;

receive, from the current-voltage measurement module, second current/voltage values measured in a state in which the second current-voltage path constitutes the bio-contact circuit, and obtain a second impedance measurement value by using the second current/voltage values;

receive, from the current-voltage measurement module, third current/voltage values measured in a state in which the third current-voltage path constitutes the bio-contact circuit, and obtain a third impedance measurement value by using the third current/voltage values;

receive, from the current-voltage measurement module, fourth current/voltage values measured in a state in which the fourth current-voltage path constitutes the bio-contact circuit, and obtain a fourth impedance measurement value by using the fourth current/voltage values;

correct the first impedance measurement value, the second impedance measurement value, the third impedance measurement value, and the fourth impedance measurement value by using the characteristic impedance value and the parasitic impedance value, so as to obtain contact impedance values of the four electrodes, respectively;

control the current-voltage path configuration module to configure a fifth current-voltage path in the bio-contact circuit such that one of two electrodes of the fifth voltage path matches with one of two electrodes of the fifth current path, and the bio-impedance is included on the fifth current path and the fifth voltage path;

receive, from the current-voltage measurement module, fifth current/voltage values measured in a state in which the fifth current-voltage path constitutes the bio-contact circuit, and obtain a fifth impedance measurement value by using the fifth current/voltage values; and acquire the bio-impedance value by using contact impedance values of electrodes located on at least the fifth voltage path among the contact impedance values, the fifth impedance measurement value, the characteristic impedance value, and the parasitic impedance value.

2. The electronic device of claim 1, further comprising a housing comprising a first surface, a second surface, and a side surface surrounding a space between the first surface and the second surface, wherein two electrodes among the four electrodes are disposed on the first surface, and the other two electrodes are disposed on the second surface.

3. The electronic device of claim 2, wherein a first electrode and a third electrode are disposed on one of the first surface and the second surface, and a second electrode and a fourth electrode are disposed on the other one of the first surface and the second surface, wherein the first current-voltage path includes a first current path established from the first electrode to the second electrode and a first voltage path established from the fourth electrode to the second electrode, wherein the second current-voltage path includes a second current path established from the third electrode to the fourth electrode and a second voltage path established from the second electrode to the fourth electrode, wherein the third current-voltage path includes a third current path established from the second electrode to the first electrode and a third voltage path established from the third electrode to the first electrode, and wherein the fourth current-voltage path includes a fourth current path established from the fourth electrode to the third electrode and a fourth voltage path established from the first electrode to the third electrode.

4. The electronic device of claim 3, wherein the instructions cause the processor to:

acquire a contact impedance value of the second electrode and a contact impedance value of the fourth electrode, by using the first impedance measurement value, the second impedance measurement value, a value of parasitic impedance caused by a parasitic component existing between the second electrode and a ground, a value of parasitic impedance caused by a parasitic component existing between the fourth electrode and the ground, a characteristic impedance value of a plurality of circuit elements connected to the second electrode, and a characteristic impedance value of a plurality of circuit elements connected to the fourth electrode, and acquire a contact impedance value of the first electrode and a contact impedance value of the third electrode, by using the third impedance measurement value, the fourth impedance measurement value, a value of parasitic impedance caused by a parasitic component existing between the first electrode and a ground, a value of parasitic impedance caused by a parasitic component existing between the third electrode and the ground, a characteristic impedance value of a plurality of circuit elements connected to the first electrode, and a characteristic impedance value of a plurality of circuit elements connected to the third electrode.

5. The electronic device of claim 4, wherein the instructions cause the processor to acquire a value of the bio-impedance, by using contact impedance values of electrodes located on the fifth voltage path, contact impedance values of electrodes that are not located on the fifth current-voltage path, a characteristic impedance value of a plurality of circuit elements connected to an electrode commonly existing on the fifth voltage path and the fifth current path, a value of parasitic impedance caused by a parasitic component existing between electrodes located on the fifth voltage path and a ground, and a value of parasitic impedance caused by a parasitic component existing between an electrode that is not located on the fifth current-voltage path and the ground.

6. The electronic device of claim 3, wherein the fifth current path and the fifth voltage path each comprise:

a current-voltage path comprising the first current path and a voltage path established from the third electrode to the second electrode;

a current-voltage path comprising the second current path and a voltage path established from the first electrode to the fourth electrode;

a current-voltage path comprising the third current path and a voltage path established from the fourth electrode to the first electrode; or a current-voltage path comprising the fourth current path and a voltage path established from the second electrode to the third electrode.

7. The electronic device of claim 1, further comprising a rectangular-shaped housing comprising a first surface, a second surface, and a side surface surrounding a space between the first surface and the second surface, wherein the four electrodes are disposed on the four corners of the side surface, respectively, wherein, when viewed from above the first surface in a state in which one of the shorter sides of the housing is oriented toward the left and the other one is oriented toward the right, two of the four electrodes are disposed on the left side, and the other two electrodes are disposed on the right side.

8. The electronic device of claim 7, wherein the first electrode and the third electrode are disposed on one of the right side and the left side, and the second electrode and fourth electrode are disposed on the other one of the right side and the left side, wherein the first current-voltage path includes a first current path established from the first electrode to the second electrode and a first voltage path established from the fourth electrode to the second electrode, wherein the second current-voltage path includes a second current path established from the third electrode to the fourth electrode and a second voltage path established from the second electrode to the fourth electrode, wherein the third current-voltage path includes a third current path established from the second electrode to the first electrode and a third voltage path established from the third electrode to the first electrode, and wherein the fourth current-voltage path includes a fourth current path established from the fourth electrode to the third electrode and a fourth voltage path established from the first electrode to the third electrode.

9. The electronic device of claim 8, wherein the instructions cause the processor to:

acquire a contact impedance value of the second electrode and a contact impedance value of the fourth electrode, by using the first impedance measurement value, the second impedance measurement value, a value of parasitic impedance caused by a parasitic component existing between the second electrode and a ground, a value of parasitic impedance caused by a parasitic component existing between the fourth electrode and the ground, a characteristic impedance value of a plurality of circuit elements connected to the second electrode, and a characteristic impedance value of a plurality of circuit elements connected to the fourth electrode; and acquire a contact impedance value of the first electrode and a contact impedance value of the third electrode, by using the third impedance measurement value, the fourth impedance measurement value, a value of parasitic impedance caused by a parasitic component existing between the first electrode and the ground, a value of parasitic impedance caused by a parasitic component existing between the third electrode and the ground, a characteristic impedance value of a plurality of circuit elements connected to the first electrode, and a characteristic impedance value of a plurality of circuit elements connected to the third electrode.

10. The electronic device of claim 9, wherein the instructions cause the processor to acquire a value of the bio-impedance, by using contact impedance values of electrodes located on the fifth voltage path, contact impedance values of electrodes that are not located on the fifth current-voltage path, a characteristic impedance value of a plurality of circuit elements connected to an electrode commonly existing on the fifth voltage path and the fifth current path, a value of parasitic impedance caused by a parasitic component existing between electrodes located on the fifth voltage path and the ground, and the value of parasitic impedance caused by a parasitic component existing between an electrode that is not located on the fifth current-voltage path and the ground.

11. The electronic device of claim 8, wherein the fifth current path and the fifth voltage path each comprise:

a current-voltage path comprising the first current path and a voltage path established from the third electrode to the second electrode;

a current-voltage path comprising the second current path and a voltage path established from the first electrode to the fourth electrode;

a current-voltage path comprising the third current path and a voltage path established from the fourth electrode to the first electrode; or a current-voltage path comprising the fourth current path and a voltage path established from the second electrode to the third electrode.

12. The electronic device of claim 1, wherein the current-voltage path configuration module comprises:

a first switch connecting the feeding port to one of the four electrodes under the control of the processor;

a second switch connecting the current measuring port to one of the four electrodes under the control of the processor;

a third switch connecting the first voltage measurement port to one of the four electrodes under the control of the processor; and a fourth switch connecting the second voltage measurement port to one of the four electrodes under the control of the processor.

13. The electronic device of claim 12, wherein the plurality of circuit elements comprises an electronic component that removes a DC component from an electrical signal flowing from the current-voltage measurement module to the bio-contact circuit.

14. The electronic device of claim 13, wherein the plurality of circuit elements comprises a first circuit element connected to the first electrode, a second circuit element connected to the second electrode, a third circuit element connected to the third electrode, and a fourth circuit element connected to the fourth electrode, wherein the first circuit element is connected to one of the feeding port, the current measurement port, the first voltage measurement port, and the second voltage measurement port by means of the first switch, wherein the second circuit element is connected to one of the feeding port, the current measurement port, the first voltage measurement port, and the second voltage measurement port by means of the second switch, wherein the third circuit element is connected to one of the feeding port, the current measurement port, the first voltage measurement port, and the second voltage measurement port by means of the third switch, and wherein the fourth circuit element is connected to one of the feeding port, the current measurement port, the first voltage measurement port, and the second voltage measurement port by means of the fourth switch.

15. The electronic device of claim 13, wherein the plurality of circuit elements comprises a first circuit element connected to the feeding port, a second circuit element connected to the current measurement port, a third circuit element connected to the first voltage measurement port, and a fourth circuit element connected to the second voltage measurement port, wherein the first circuit element is connected to one of the four electrodes by means of the first switch, wherein the second circuit element is connected to one of the four electrodes by means of the second switch, wherein the third circuit element is connected to one of the four electrodes by means of the third switch, and wherein the fourth circuit element is connected to one of the four electrodes by means of the fourth switch.

* * * * *